United States Patent
Hampapuram et al.

(10) Patent No.: US 12,190,010 B2
(45) Date of Patent: *Jan. 7, 2025

(54) CONTINUOUS GLUCOSE MONITOR COMMUNICATION WITH MULTIPLE DISPLAY DEVICES

(71) Applicant: Dexcom, Inc., San Diego, CA (US)

(72) Inventors: Hari Hampapuram, Beaverton, OR (US); Eric Cohen, San Diego, CA (US); Brian Christopher Smith, San Marcos, CA (US); Jose Hector Hernandez-Rosas, San Diego, CA (US); Francis William Pascual, San Diego, CA (US); Michael Robert Mensinger, San Diego, CA (US); Shawn Larvenz, Ramona, CA (US)

(73) Assignee: Dexcom, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/470,092

(22) Filed: Sep. 19, 2023

(65) Prior Publication Data
US 2024/0012602 A1    Jan. 11, 2024

Related U.S. Application Data

(63) Continuation of application No. 17/814,215, filed on Jul. 21, 2022, now Pat. No. 11,797,250, which is a (Continued)

(51) Int. Cl.
G06F 3/14 (2006.01)
A61B 5/00 (2006.01)
(Continued)

(52) U.S. Cl.
CPC .......... *G06F 3/1423* (2013.01); *A61B 5/0004* (2013.01); *A61B 5/14532* (2013.01); (Continued)

(58) Field of Classification Search
CPC ......... H04L 67/12; H04L 67/10; H04L 67/34; H04L 9/30; H04L 67/125; H04L 2209/88;
(Continued)

(56) References Cited

U.S. PATENT DOCUMENTS

| 2 A * | 7/1836 | Goulding ............... D01G 21/00 |
| | | 57/58.49 |
| 6,219,669 B1 * | 4/2001 | Haff ........................ H04L 67/14 |

(Continued)

FOREIGN PATENT DOCUMENTS

| CA | 2690742 A1 | 12/2008 |
| CN | 1885770 A | 12/2006 |

(Continued)

OTHER PUBLICATIONS

International Preliminary Report on Patentability for Application No. PCT/US2016/014145 mailed on Aug. 3, 2017, 13 pages.
(Continued)

*Primary Examiner* — Sharif E Ullah
(74) *Attorney, Agent, or Firm* — Patterson + Sheridan, LLP

(57) ABSTRACT

A continuous glucose monitor for wirelessly transmitting data relating to glucose value to a plurality of displays is disclosed, as well as systems and methods for limiting the number of display devices that can connect to a continuous glucose transmitter. In addition, security, including hashing techniques and a changing application key, can be used to provide secure communications between the continuous glucose transmitter and the displays. Also provided is a continuous glucose monitor and techniques for authenticating multiple displays, providing secure data transmissions to multiple displays, and coordinating the interaction of commands and data updates between multiple displays.

26 Claims, 19 Drawing Sheets

Related U.S. Application Data continuation of application No. 16/198,651, filed on Nov. 21, 2018, now Pat. No. 11,429,334, said application No. 15/002,155 is a continuation of application No. 15/001,756, filed on Jan. 20, 2016, now Pat. No. 10,359,983, said application No. 16/198,651 is a continuation of application No. 15/002,155, filed on Jan. 20, 2016, now Pat. No. 10,168,974.

(60) Provisional application No. 62/106,150, filed on Jan. 21, 2015.

(51) Int. Cl.
    *A61B 5/145*     (2006.01)
    *G09G 5/00*     (2006.01)
    *G16H 40/63*     (2018.01)
    *G16Z 99/00*     (2019.01)
    *H04W 76/11*     (2018.01)
    *H04W 76/14*     (2018.01)

(52) U.S. Cl.
CPC ............ *A61B 5/742* (2013.01); *A61B 5/7445* (2013.01); *G06F 3/1454* (2013.01); *G09G 5/003* (2013.01); *G16H 40/63* (2018.01); *G16Z 99/00* (2019.02); *H04W 76/11* (2018.02); *H04W 76/14* (2018.02); *G09G 2358/00* (2013.01); *G09G 2370/16* (2013.01); *G09G 2380/08* (2013.01)

(58) Field of Classification Search
CPC ...... H04L 63/10; H04L 43/065; H04W 12/06; H04W 76/10; H04W 12/50; H04W 12/08; H04W 12/04; H04W 88/02; H04W 12/71; H04W 76/14; G06F 21/6245; G06F 3/04847; G06F 8/61; G06F 8/60; G06F 21/31; G06F 3/0619; G06F 3/065; G06F 3/1423
USPC ............. 345/2; 726/2, 21, 36; 713/150, 163, 713/181; 380/255, 264, 276
See application file for complete search history.

(56) References Cited

U.S. PATENT DOCUMENTS

| | | | |
|---|---|---|---|
| 7,660,422 B2 | 2/2010 | Mitchell et al. | |
| 7,928,850 B2 | 4/2011 | Hayter et al. | |
| 8,407,759 B1* | 3/2013 | Sotos | G06F 21/78 455/39 |
| 8,589,690 B2* | 11/2013 | Kassai | H04L 9/0844 713/176 |
| 8,644,823 B2* | 2/2014 | Rozinov | H04L 61/4535 709/227 |
| 8,686,216 B2* | 4/2014 | Wattebled | A61L 15/60 514/159 |
| 8,803,688 B2 | 8/2014 | Halff et al. | |
| 8,844,007 B2* | 9/2014 | Vicente | G16H 10/40 713/168 |
| 8,854,206 B2* | 10/2014 | Kai | G16Z 99/00 600/300 |
| 9,094,379 B1* | 7/2015 | Miller | H04L 9/14 |
| 9,143,569 B2* | 9/2015 | Mensinger | G16H 40/67 |
| 9,241,768 B2* | 1/2016 | Sandhu | A61B 34/76 |
| 9,386,522 B2 | 7/2016 | San Vicente et al. | |
| 9,603,024 B2 | 3/2017 | Wang et al. | |
| 9,825,961 B2 | 11/2017 | Etter et al. | |
| 9,931,036 B2 | 4/2018 | Miller et al. | |
| 10,007,473 B2* | 6/2018 | Hampapuram | G06F 3/1454 |
| 10,168,974 B2 | 1/2019 | Hampapuram et al. | |
| 10,359,983 B2 | 7/2019 | Hampapuram et al. | |
| 2004/0078449 A1* | 4/2004 | Tanaka | H04L 67/01 709/201 |
| 2004/0117858 A1* | 6/2004 | Boudreau | H04N 21/8133 348/E5.005 |
| 2005/0235345 A1* | 10/2005 | Mitchell | H04L 9/083 726/10 |
| 2006/0001551 A1* | 1/2006 | Kraft | A61B 5/14532 128/903 |
| 2008/0278331 A1* | 11/2008 | Hayter | A61B 5/0022 600/347 |
| 2008/0298375 A1* | 12/2008 | Agardh | H04L 63/065 455/84 |
| 2009/0240120 A1* | 9/2009 | Mensinger | G16H 40/63 600/301 |
| 2011/0163881 A1* | 7/2011 | Halff | G16H 40/67 340/573.1 |
| 2012/0078071 A1* | 3/2012 | Bohm | G06F 1/3203 600/345 |
| 2013/0017791 A1* | 1/2013 | Wang | H04W 4/80 455/41.2 |
| 2013/0078912 A1* | 3/2013 | San Vicente | A61B 5/0026 455/39 |
| 2013/0231711 A1* | 9/2013 | Kaib | G16H 20/30 607/5 |
| 2014/0266776 A1* | 9/2014 | Miller | A61B 5/0015 340/870.01 |
| 2014/0313052 A1* | 10/2014 | Yarger | G16Z 99/00 340/870.02 |
| 2015/0123811 A1* | 5/2015 | Hernandez-Rosas | H04Q 9/14 340/870.02 |
| 2016/0034764 A1* | 2/2016 | Connor | G06V 20/52 348/158 |
| 2016/0050212 A1* | 2/2016 | Etter | G06F 21/629 726/28 |
| 2018/0027105 A1* | 1/2018 | Mandapaka | H04W 76/25 455/41.3 |
| 2018/0110077 A1* | 4/2018 | Mandapaka | H04W 76/23 |
| 2019/0095165 A1 | 3/2019 | Hampapuram et al. | |

FOREIGN PATENT DOCUMENTS

| | | |
|---|---|---|
| CN | 102594987 A | 7/2012 |
| CN | 103930029 A | 7/2014 |
| CN | 104320161 A | 1/2015 |
| JP | 2009055428 A | 3/2009 |
| JP | 2010507928 A | 3/2010 |
| JP | 2012105100 A | 5/2012 |
| JP | 2013502978 A | 1/2013 |
| JP | 2013172259 A | 9/2013 |
| KR | 20140129759 A | 11/2014 |
| WO | 2013044153 A1 | 3/2013 |
| WO | 2014099012 A1 | 6/2014 |
| WO | 2014188827 A1 | 11/2014 |

OTHER PUBLICATIONS

International Search Report and Written Opinion for Application No. PCT/US2016/014145 mailed on Jun. 27, 2016, 17 pages.

\* cited by examiner

CONTINUOUS GLUCOSE MONITOR COMMUNICATION WITH MULTIPLE DISPLAY DEVICES

INCORPORATION BY REFERENCE TO RELATED APPLICATIONS

This application is a continuation of U.S. patent application Ser. No. 17/814,215, filed Jul. 21, 2022, which is a continuation of U.S. patent application Ser. No. 16/198,651, filed Nov. 21, 2018, now issued as U.S. Pat. No. 11,429,334, which is a continuation of U.S. patent application Ser. No. 15/002,155, filed Jan. 20, 2016, now issued as U.S. Pat. No. 10,168,974, which is a continuation of U.S. application Ser. No. 15/001,756, filed Jan. 20, 2016, now issued as U.S. Pat. No. 10,359,983, which claims the benefit of U.S. Provisional Application No. 62/106,150, filed Jan. 21, 2015. Each of the aforementioned applications is incorporated by reference herein in its entirety, and each is hereby expressly made a part of this specification.

TECHNICAL FIELD

The present disclosure relates to a continuous glucose sensor that transmits data relating to glucose levels to multiple displays in a secure fashion.

BACKGROUND

Continuous glucose monitors have been increasing in popularity as an easy way to monitor glucose levels. In the past, users sample their blood glucose levels several times throughout a day, such as in the morning, around lunch, and in the evening. The levels can be measured by taking a small blood sample and measuring the glucose levels with a test strip or blood glucose meter. This technique, however, has drawbacks because users would prefer to not have to take a blood sample, and users do not know what their glucose levels are throughout the day between the samples.

One potentially dangerous timeframe is at night because a user's glucose levels can fall dangerously low during sleep. As a result, continuous glucose monitors have gained popularity by providing a sensor that continuously monitors glucose levels and transmits the glucose levels wirelessly to a display. This allows the user to monitor their glucose levels throughout the day and even set alarms for when glucose levels reach a predefined level or experience a defined change.

Initially, continuous glucose monitors wirelessly transmitted data relating to glucose levels to a receiver acting as a dedicated display. The dedicated display can be a medical device designed to display glucose levels, trending patterns, and other information for a user. However, with the increasing popularity of smart phones and applications executing on smart phones, some users prefer to avoid having to carry a dedicated display. Instead, users would prefer to monitor their glucose levels using an application executing on a smartphone, alone or along with a dedicated display.

The present disclosure is directed to overcoming these and other problems.

SUMMARY

The disclosure relates to allowing users to carry and monitor glucose levels using a plurality of displays, such as a dedicated display associated with a continuous glucose monitor system and a smart phone, tablet, personal computer, or other device. Users can carry two displays and monitor glucose levels with different displays at different times. For example, a user may use their smart phone application sometimes, but then their smart phone application may be turned off and the user will switch to using a dedicated display. The disclosed system coordinates the transmission and display of the same data on two separate displays to ensure consistency. Commands from both displays can be received and processed in a timely fashion, and both displays can display the same data.

In other embodiments, a user can send commands from the dedicated display, the smart phone, or both to control the continuous glucose monitor system. Given the timing of when a user enters a command on a particular display, the two displays may actually display different data. For example, a user may enter a calibration command on a first display that is only processed after the current glucose data has been sent to a second display. The first display will therefore display different glucose levels based on the new calibration, while the second display will continue to display old data. Systems and methods described below ensure consistency of data display across multiple devices.

In addition, the disclosure provides for secure communications within the system. Medical devices wirelessly transmit sensitive medical data for a patient. Ensuring that communications only occur between approved, authenticated devices can be a key to offering users an appropriate level of security given the sensitive nature of the data being transmitted. Broadcasting glucose readings and related information between a glucose sensor and transmitter can compromise the data without authentication or other techniques for securing communications. For example, a second user's display may receive glucose data for another user, causing confusion and a breach of privacy. There is therefore a need for secure communications between a glucose sensor and multiple displays. Examples of securing communications include requiring an authentication protocol before a device can use data, and using encryption to prevent unauthorized access.

Transmitting glucose data to multiple displays also places a strain on the battery of the glucose sensor and transmitter. Each display should be authenticated, paired, and receive the data, which compounds communications as additional displays are added. Therefore, in some embodiments, the number of displays that can connect to a particular transmitter at any given time can be limited. Users should also be able to add or remove a given display from being able to communicate with the glucose sensor.

In one exemplary embodiment, a method for pairing a transmitter of a continuous glucose monitoring system with a plurality of display devices is disclosed. The method may include connecting a first display device to the transmitter over a first wireless connection, connecting a second display device to the transmitter over a second wireless connection, and limiting the number of display devices connected to the transmitter by rejecting additional connection requests during a communication interval. The method may also include exchanging an application key with the first display device and the second display device periodically, the application key changing at the beginning of each period.

In another embodiment, a system for pairing a transmitter of a continuous glucose monitoring system with a plurality of display devices is disclosed. The system may include a first display device configured to connect with the transmitter over a first wireless connection and a second display device configured to connect with the transmitter over a second wireless connection. The transmitter can be configured to limit the number of connected display devices by rejecting additional connection requests during a communication interval, and exchange an application key with the first display device and the second display device periodically, the application key changing at the beginning of each period.

A computer-readable medium is also disclosed comprising instructions which, when executed by one or more processors, perform a method for pairing a transmitter of a continuous glucose monitoring system with a plurality of display devices. The method may include connecting a first display device to the transmitter over a first wireless connection, connecting a second display device to the transmitter over a second wireless connection, and limiting the number of display devices connected to the transmitter by rejecting additional connection requests during a communication interval. It also includes exchanging an application key with the first display device and the second display device periodically, the application key changing at the beginning of each period.

In another embodiment, a method for pairing a transmitter of a continuous glucose monitoring system with a display device is disclosed that includes receiving a first identifier from the display device, creating a first hashed value by executing a hash algorithm on the first identifier, receiving an advertisement signal from the transmitter, parsing at least one of the advertisement signal or signals associated with the advertisement signal to identify a second hashed value, the second hashed value comprising a portion of a transmitter identifier associated with the transmitter, comparing the first hashed value and the second hashed value, denying connection between the transmitter and the display device when the first hashed value and the second hashed value do not match, and allowing connection between the transmitter and the display device when the first hashed value and the second hashed value match.

In another embodiment, one or more computer-readable media are disclosed comprising instructions which, when executed by one or more processors, perform a method for pairing a transmitter of a continuous glucose monitoring system with a display device. The method may include receiving a first identifier from the display device, creating a first hashed value by executing a hash algorithm on the first identifier, receiving an advertisement signal from the transmitter, parsing at least one of the advertisement signal or signals associated with the advertisement signal to identify a second hashed value, the second hashed value comprising a portion of a transmitter identifier associated with the transmitter, comparing the first hashed value and the second hashed value, denying connection between the transmitter and the display device when the first hashed value and the second hashed value do not match, and allowing connection between the transmitter and the display device when the first hashed value and the second hashed value match.

In another embodiment, a system is disclosed for pairing a transmitter of a continuous glucose monitoring system with a display device. The system includes a wireless receiver in the first display device configured to receive a first identifier, and a processor in the first display device configured to create a first hashed value by executing a hash algorithm on the first identifier, receive an advertisement signal from the transmitter, parse at least one of the advertisement signal or signals associated with the advertisement signal to identify a second hashed value, the second hashed value comprising a portion of a transmitter identifier associated with the transmitter, compare the first hashed value and the second hashed value, deny connection between the transmitter and the display device when the first hashed value and the second hashed value do not match, and allow connection between the transmitter and the display device when the first hashed value and the second hashed value match.

In another embodiment, a method is disclosed for pairing a transmitter of a continuous glucose monitoring system with a display device. The method includes receiving an advertisement signal from the transmitter, establishing a connection between the transmitter and the display device, receiving a first key from the transmitter, comparing the first key with a second key stored by the display device, authenticating the transmitter with the display device when the first key matches the second key, transmitting, after authenticating, an application key from the display device to the transmitter, receiving acceptance of the application key from the transmitter, allowing communication between the transmitter and the display device after receiving acceptance of the application key, transmitting data relating to continuous glucose values from the transmitter to the display device, creating, by the display device after an amount of time, a second application key, transmitting the second application key from the display device to the transmitter, receiving acceptance of the second application key from the transmitter, and allowing further communication between the transmitter and the display device after receiving acceptance of the new application key.

In another embodiment, one or more computer-readable media are disclosed comprising instructions which, when executed by one or more processors, perform a method for pairing a transmitter of a continuous glucose monitoring system with a display device, the method comprising receiving an advertisement signal from the transmitter, establishing a connection between the transmitter and the display device, receiving a first key from the transmitter, comparing the first key with a second key stored by the display device, authenticating the transmitter with the display device when the first key matches the second key, transmitting, after authenticating, an application key from the display device to the transmitter, receiving acceptance of the application key from the transmitter, allowing communication between the transmitter and the display device after receiving acceptance of the application key, transmitting data relating to continuous glucose values from the transmitter to the display device, creating, by the display device after an amount of time, a second application key, transmitting the second application key from the display device to the transmitter, receiving acceptance of the second application key from the transmitter, and allowing further communication between the transmitter and the display device after receiving acceptance of the new application key.

In another embodiment, a system is disclosed for pairing a transmitter of a continuous glucose monitoring system with a display device. The system includes a transmitter configured to transmit an advertisement signal, a display device configured to establish a connection with the transmitter based on the advertisement signal, a wireless receiver in the display device configured to receive a first key from the transmitter, memory in the display device configured to store a second key, and a processor in the display device. The processor can compare the first key with a second key, authenticate the transmitter with the display device when the first key matches the second key, transmit, after authenticating, an application key to the transmitter, receive acceptance of the application key from the transmitter, allow communication with the transmitter after receiving acceptance of the application key, receive data relating to continuous glucose values from the transmitter, create, after an amount of time, a second application key, transmit the second application key to the transmitter, receive acceptance of the second application key from the transmitter, and allow further communication between the transmitter and the display device after receiving acceptance of the new application key.

In another embodiment, a method is disclosed for establishing communication between a plurality of display devices and a transmitter of a continuous glucose monitoring system. The method includes receiving a request to connect the transmitter with a first display device, the request identifying a first type of the first display device, comparing the first type of the first display device with a list including a plurality of allowed types of display devices, determining whether a display device having the first type is actively connected with the transmitter, connecting the transmitter with the first display device when fewer than a predetermined number of display devices with the first type are included in the list, receiving a request to connect the transmitter with a second display device, the request identifying a second type of the second display device, comparing the second type of the second display device with the list including a plurality of allowed types of display devices, determining whether a display device having the second type is actively connected with the transmitter, and connecting the transmitter with the second display device when fewer than the predetermined number of display devices with the second type are included in the list.

In another embodiment, one or more computer-readable media are disclosed comprising instructions which, when executed by one or more processors, perform a method for establishing communication between a plurality of display devices and a transmitter of a continuous glucose monitoring system. The method may include receiving a request to connect the transmitter with a first display device, the request identifying a first type of the first display device, comparing the first type of the first display device with a list including a plurality of allowed types of display devices, determining whether a display device having the first type is actively connected with the transmitter, connecting the transmitter with the first display device when fewer than a predetermined number of display devices with the first type are included in the list, receiving a request to connect the transmitter with a second display device, the request identifying a second type of the second display device, comparing the second type of the second display device with the list including a plurality of allowed types of display devices, determining whether a display device having the second type is actively connected with the transmitter, and connecting the transmitter with the second display device when fewer than the predetermined number of display devices with the second type are included in the list.

In another embodiment, a system is disclosed for establishing communication between a plurality of display devices and a transmitter of a continuous glucose monitoring system. The system includes a first display device, a second display device, a wireless receiver in the transmitter configured to receive a request to connect the transmitter with a first display device, the request identifying a first type of the first display device, a memory in the transmitter configured to store a list of allowed types of display devices, and a processor in the transmitter. The processor can compare the first type of the first display device with the list, determine whether a display device having the first type is actively connected with the transmitter, connect the transmitter with the first display device when fewer than a predetermined number of display devices with the first type are included in the list, receive a request to connect the transmitter with a second display device, the request identifying a second type of the second display device, compare the second type of the second display device with the list including a plurality of allowed types of display devices, determine whether a display device having the second type is actively connected with the transmitter, and connect the transmitter with the second display device when fewer than the predetermined number of display devices with the second type are included in the list.

In another embodiment, a method for establishing communication between a plurality of display devices and a transmitter of a continuous glucose monitoring system is disclosed. The method may include creating a list of approved devices, the list including a plurality of types of devices, executing an authentication process with a first display device and the transmitter, the authentication process including receiving an identifier of the type of the first display device, adding the first display device to the list of approved devices, executing the authentication process with a second display device and the transmitter, the authentication process including receiving an identifier of the type of the second device, the type of the second device being different from the type of the first device, adding the second display device to the list of approved devices, receiving a request to remove the first display device from the list, removing the first display device from the list of approved devices, executing the authentication process with a third display device and the transmitter, the authentication process including receiving an identifier of the type of third device, the type of the third device being the same as the type of the first device, and adding the third display device to the list of approved devices.

In another embodiment, one or more computer-readable media are disclosed comprising instructions which, when executed by one or more processors, perform a method for establishing communication between a plurality of display devices and a transmitter of a continuous glucose monitoring system. The method may include creating a list of approved devices, the list including a plurality of types of devices, executing an authentication process with a first display device and the transmitter, the authentication process including receiving an identifier of the type of the first display device, adding the first display device to the list of approved devices, executing the authentication process with a second display device and the transmitter, the authentication process including receiving an identifier of the type of the second device, the type of the second device being different from the type of the first device, adding the second display device to the list of approved devices, receiving a request to remove the first display device from the list, removing the first display device from the list of approved devices, executing the authentication process with a third display device and the transmitter, the authentication process including receiving an identifier of the type of third device, the type of the third device being the same as the type of the first device, and adding the third display device to the list of approved devices.

In another embodiment, a system is disclosed for establishing communication between a plurality of display devices and a transmitter of a continuous glucose monitoring system. The system includes a first display device, a second display device, a memory associated with the transmitter, the memory configured to store a list of approved devices, the list including a plurality of device types, and a processor associated with the transmitter. The processor can execute an authentication process with a first display device and the transmitter, the authentication process including receiving an identifier of the type of the first display device, add the first display device to the list of approved devices, execute the authentication process with a second display device and the transmitter, the authentication process including receiving an identifier of the type of the second device, the type of the second device being different from the type of the first device, add the second display device to the list of approved devices, receive a request to remove the first display device from the list, remove the first display device from the list of approved devices, execute the authentication process with a third display device and the transmitter, the authentication process including receiving an identifier of the type of third device, the type of the third device being the same as the type of the first device, and add the third display device to the list of approved devices.

In another embodiment, a method for exchanging commands between a transmitter of a continuous glucose monitoring system and one or more display devices is disclosed. The method includes placing the transmitter in an idle state, receiving a command at a first display device, the command requiring exchange of data with the transmitter, placing the first display device in an intermediate state depending on a type of the command, transitioning the transmitter from the idle state to an active state, transmitting the command from the first display device to the transmitter, receiving a response including updated data relating to control of the transmitter from the transmitter, removing the first display device from the intermediate state, and displaying the updated data by the first display.

In another embodiment, one or more computer-readable media are disclosed comprising instructions which, when executed by one or more processors, perform a method for exchanging commands between a transmitter of a continuous glucose monitoring system and one or more display devices. The method includes placing the transmitter in an idle state, receiving a command at a first display device, the command requiring exchange of data with the transmitter, placing the first display device in an intermediate state depending on a type of the command, transitioning the transmitter from the idle state to an active state, transmitting the command from the first display device to the transmitter, receiving a response including updated data relating to control of the transmitter from the transmitter, removing the first display device from the intermediate state, and displaying the updated data by the first display.

In another embodiment, a system is disclosed for exchanging commands between a transmitter of a continuous glucose monitoring system and one or more display devices. The system includes a first display device configured to receive a command requiring exchange of data with the transmitter and place the first display device in an intermediate state depending on a type of the command. The system also includes a processor associated with the transmitter, the processor configured to place the transmitter in an idle state for a period of time, transition the transmitter from the idle state to an active state, receive, during the active state, the command from the first display device, and transmit a response to the first display device, the response including updated data relating to control of the transmitter from the transmitter. In response to receiving the response, the first display device ends the intermediate state by displaying the updated data.

In another embodiment, a method is disclosed for synchronizing data displayed on a first display device and a second display device. The method includes connecting the first display device with a transmitter of a continuous glucose monitoring system, connecting the second display device with the transmitter, allowing transmission of commands to the transmitter at specified times, receiving, by the first display device and the second display device, data relating to glucose levels from the transmitter, receiving, at the first display device, a command relating to calibration of a continuous glucose sensor, transmitting the command relating to calibration to the continuous glucose sensor at one of the specified times, calculating, based on the command relating to calibration, data relating to updated glucose levels, and transmitting the data relating to updated glucose levels to the first display device and the second display device.

In another embodiment, one or more computer-readable media are disclosed comprising instructions which, when executed by one or more processors, perform a method for synchronizing data displayed on a first display device and a second display device. The method includes connecting the first display device with a transmitter of a continuous glucose monitoring system, connecting the second display device with the transmitter, allowing transmission of commands to the transmitter at specified times, receiving, by the first display device and the second display device, data relating to glucose levels from the transmitter, receiving, at the first display device, a command relating to calibration of a continuous glucose sensor, transmitting the command relating to calibration to the continuous glucose sensor at one of the specified times, calculating, based on the command relating to calibration, data relating to updated glucose levels, and transmitting the data relating to updated glucose levels to the first display device and the second display device.

In another embodiment, a continuous glucose sensor is configured to synchronize data displayed on a first display device and a second display device. The sensor includes a wireless transceiver configured to wirelessly connect with the first display device and the second display device, and a processor. The processor can transmit data relating to glucose levels to the first display device and the second display device, receive a command relating to calibration of the continuous glucose sensor at a specified time, calculate, based on the command relating to calibration, data relating to updated glucose levels, and transmit the data relating to updated glucose levels to the first display device and the second display device.

In another embodiment, a method for connecting a transmitter of a continuous glucose system with a plurality of displays. The method includes advertising, by the transmitter, at a defined communication interval, receiving, in response to the advertising, requests from a first display and a second display to connect with the transmitter, determining whether to authorize connections with the first display and the second display based a device type for the first display and a device type for the second display, executing an authentication process to pair the first display and the second display with the transmitter when the connections are authorized, and storing bonding information associated with the authentication process in memory.

In another embodiment, a system is disclosed for connecting a transmitter of a continuous glucose system with a plurality of displays. The transmitter is configured to receive, in response to the advertising, requests from a first display and a second display to connect with the transmitter, determine whether to authorize connections with the first display and the second display based a device type for the first display and a device type for the second display, execute an authentication process to pair the first display and the second display with the transmitter when the connections are authorized, and store bonding information associated with the authentication process in memory.

In another embodiment, a computer-readable medium comprising instructions which, when executed by a processor, perform a method for connecting a transmitter of a continuous glucose system with a plurality of displays. The method includes advertising, by the transmitter, at a defined communication interval, receiving, in response to the advertising, requests from a first display and a second display to connect with the transmitter, determining whether to authorize connections with the first display and the second display based a device type for the first display and a device type for the second display, executing an authentication process to pair the first display and the second display with the transmitter when the connections are authorized, and storing bonding information associated with the authentication process in memory.

Other systems, methods, features and/or advantages will be or may become apparent to one with skill in the art upon examination of the following drawings and detailed description. It is intended that all such additional systems, methods, features and/or advantages be included within this description and be protected by the accompanying claims.

DETAILED DESCRIPTION

The present disclosure relates to a continuous glucose monitor and techniques for authenticating multiple displays, providing secure data transmissions to multiple displays, and coordinating the interaction of commands and data updates between multiple displays.

Figure 1:
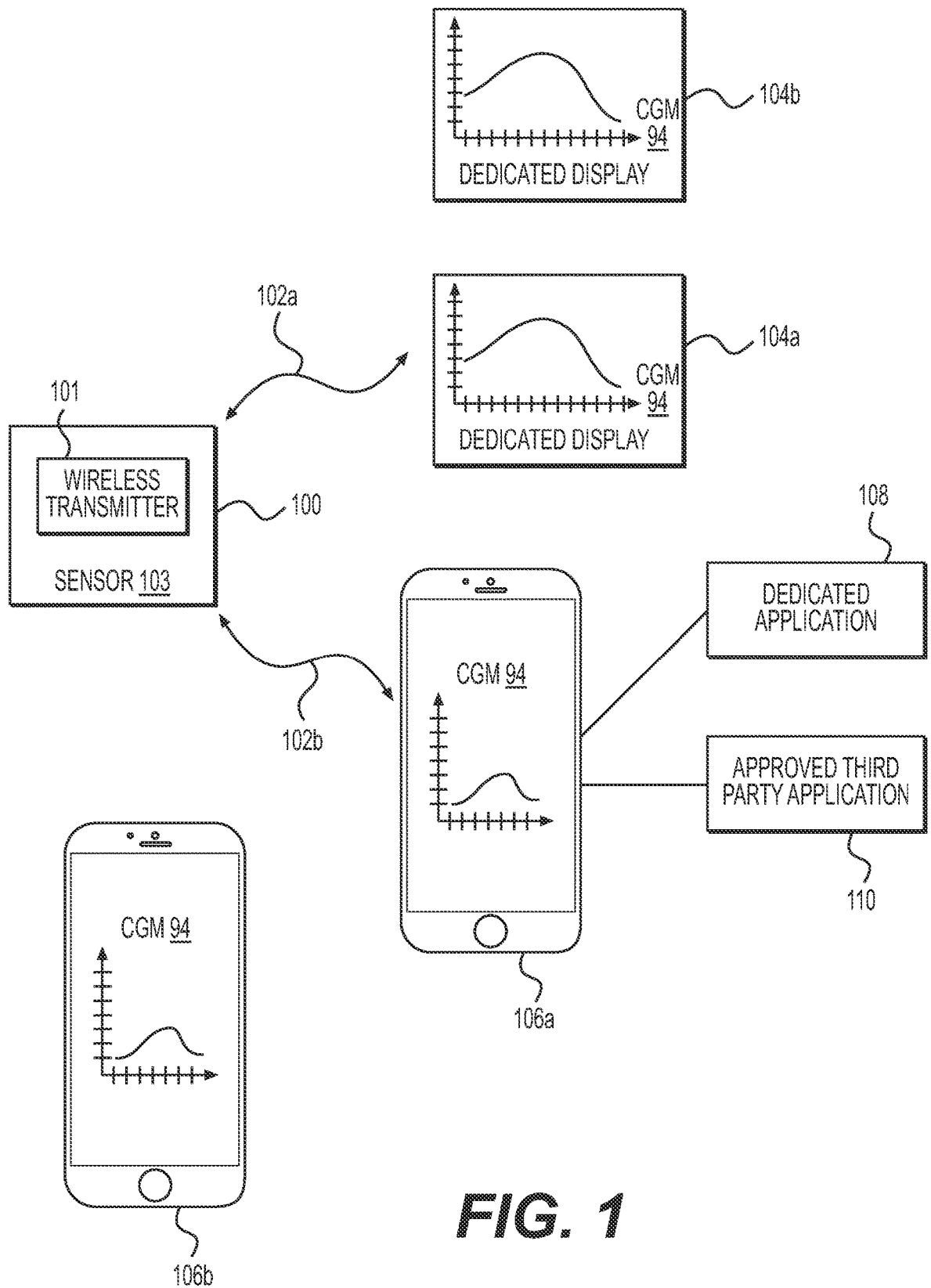
FIG. 1 illustrates an exemplary system for monitoring glucose levels.

FIG. 1 illustrates an exemplary system for monitoring glucose levels. With reference to FIG. 1, continuous glucose sensor system 100 obtains a series of measurements relating to glucose levels in a user. The continuous glucose sensor system 100 can be worn, for example, in the abdomen region of a patient. A small sensor 103 can be placed on or into the patient to obtain readings of glucose values using, for example, subcutaneous glucose or blood glucose readings. The sensor can be placed into the patient using a needle that extends into the patient, deposits the sensor, and then retracts and can be discarded. An applicator or other similar device can contain the needle and be used for inserting the sensor. The continuous glucose sensor system 100 can also be a transdermal device, an intravascular device, or a non-invasive device.

Continuous glucose sensor system 100 may include a number of components to obtain glucose measurements, store the data, calculate glucose levels, communicate with dedicated display 104a and display 106a, and perform other tasks. For example, although not illustrated, continuous glucose sensor system 100 may include nonvolatile memory for storing historical data regarding glucose values, a processor, a battery, and a wireless transmitter 101. The wireless transmitter 101 may provide any type of wireless communications 102a and 102b, including a Bluetooth connection, WiFi connection, RF connection, and others. The wireless communications 102a and 102b may occur, in some embodiments, between paired, authenticated devices, and may use encryption and other cryptographic techniques to ensure that communications remain confidential.

While illustrated as a single unit, the wireless transmitter 101 may be removable from the continuous glucose sensor system 100 and reusable with multiple sensors 103 as the sensors 103 are replaced. Further, the continuous glucose sensor system 100 can include other components to facilitate data communications. For example, the continuous glucose sensor system 100 may include wired ports, such as a USB port, Ethernet port, and others, for communicating with other devices and providing data relating to glucose levels. The continuous glucose sensor system 100 may include the processing circuitry, such as a processor, memory, and a battery, as part of the sensor electronics. The sensor electronics may be included in the continuous glucose sensor system 100 or the transmitter 101. The sensor portion 103 of the continuous glucose sensor system 100 may be removable and replaceable, allowing a patient to change to a new sensor periodically, such as every week. Similarly, the transmitter 101 may detach and be removable from the continuous glucose sensor system 100, allowing replacement as needed, such as every six months.

Continuous glucose sensor system 100 may obtain samples at predetermined intervals, such as every few seconds, every thirty seconds, every minute, or on demand in response to a command from a user. In one embodiment, the wireless transmitter can be turned off to conserve battery life, and measurements taken over a period of time can be wirelessly transmitted to dedicated display 104a and display 106a in a batch transfer. For example, the continuous glucose sensor system 100 can wake up the wireless transmitter every five minutes, transfer data relating to glucose measurements taken over the last five minutes, and transfer the data to the dedicated display 104a and display 106a. The wireless transmitter 101 can then be turned off again to conserve battery life. While an example of transferring data every five minutes has been provided, it will be appreciated that longer or shorter time periods can be used, and the time period can be configured by a user via dedicated display 104a or display 106a.

The system of FIG. 1 may have a state determined by the continuous glucose sensor system 100 and its transmitter 101. One exemplary system state includes not started, such as when a sensor 103 has not yet been inserted into the host or when the user has not yet activated the continuous glucose sensor system 100. Another example is a sensor warm-up period, which may last for a period of time, such as two hours, when the sensor 103 is warming up and acclimating to insertion in the user's body. The sensor warm-up state may also include a calibration period. Other examples of system states include in calibration or out of calibration. A sensor 103 and/or continuous glucose sensor system 100 may be in calibration when it has been calibrated within a predetermined interval, such as within the last twelve hours, and out of calibration if a predetermined duration (e.g. twelve hours) has passed since the last calibration. Another exemplary system state is sensor stopped. The sensor stopped state may occur, for example, when a user seeks to replace the sensor portion 103 of the glucose sensor system 100.

The system of FIG. 1 coordinates communication among continuous glucose sensor system 100, dedicated display 104a, and display 106a to ensure consistent operations. The continuous glucose sensor system 100 may advertise and communicate with the displays in communication periods that occur at intervals. Advertising is a process of the continuous glucose sensor system 100 broadcasting its presence to look for other devices to connect with. Optionally, the communication intervals may occur about every five minutes (for instance, the communication interval may last 30 seconds, so the interval would occur four and a half minutes after the end of each communication interval). During the communication interval, the continuous glucose sensor system 100 may exchange data relating to glucose levels, system configuration information, system status information, patient identifying information, and other information with the displays. The displays may receive these data transmissions and also send commands to the continuous glucose sensor system 100. The transmitter 101 in the continuous glucose sensor system 100 may update the system state in response to a command and transmit a message with the updated system state to the connected displays.

There is a possibility of mismatched values being displayed by the two displays in the situation where one display has already communicated during a communication interval, and then the second display updates calibration values. In this example, the first display will continue to present to a user the old values based on the prior calibration until it is updated during the next communication interval. To illustrate, a user may enter a command, such as a calibration command, into display 106a, and that command will be sent to the continuous glucose sensor system 100 during the next communication interval. If in the next communication interval, the continuous glucose sensor system 100 first communicates with dedicated display 104a by providing, for example, data relating to glucose levels over the last five minutes, the dedicated display 104a will present that glucose data to the user. However, if the continuous glucose sensor system 100 next communicates with display 106a and receives a calibration command, the continuous glucose sensor system 100 may then calculate new glucose levels. This can lead to mismatched values being displayed on dedicated display 104a and display 106a. Other scenarios also include starting or stopping a sensor when a user wants to replace the sensor. As a result, the system of FIG. 1 may coordinate the transmission of commands and data relating to glucose levels among continuous glucose sensor system 100, dedicated display 104a, and display 106a to ensure consistent operation. Exemplary embodiments will be described in more detail below in, for example, FIGS. 11, 12, and 17.

The data transmitted from continuous glucose sensor system 100 to dedicated display 104a and display 106a may be any type of data relating to monitoring glucose values. For example, the continuous glucose sensor system 100 may exchange calibration data with dedicated display 104a and 106a on initial startup and periodically thereafter to maintain accuracy of the glucose measurements. A user may measure their glucose level using a blood glucose meter, enter the value displayed by the meter, and that value may be used to calibrate the continuous glucose sensor system 100. Multiple samples from a blood glucose meter may be used to promote accuracy and proper calibration. Other examples of transmitted data include an amount of current or voltage measured by continuous glucose sensor, a converted glucose value in, for example, mg/dL, and a timestamp associated with the time when each measurement or value was sampled, diagnostic data, and the like. Although described as a continuous glucose sensor system 100, other medical devices may be used with the disclosed embodiments. For example, the continuous glucose sensor system 100 may an analyte sensor and the transmitted data may reflect analyte values.

Dedicated display 104a may be a display dedicated to use with continuous glucose sensor system 100. The combination of the continuous glucose sensor system 100 and dedicated display 104a may, in one embodiment, be approved medical devices, such as a class III medical device. Dedicated display 104a may receive data relating to glucose levels from continuous glucose sensor system 100 in real-time, which includes both continuous streaming of data and batched data transmission.

Because dedicated display 104a is part of an approved medical device with continuous glucose sensor system 100, dedicated display 104a may, in one embodiment, receive and display the enhanced set of data received from continuous glucose sensor system 100 relative to other displays or third-party applications or system components. For example, dedicated display 104a can display actual glucose levels associated with measurements taken by the sensor. In contrast, third-party applications executing on display 106a may be restricted from receiving and displaying actual glucose levels and instead may receive a more generic indicator of glucose levels, such as whether glucose levels are low, normal, or high. Additional details regarding the types of data that can be sent to and displayed by dedicated display 104a and display 106a will be provided below.

Dedicated display 104a may include a processor for calculating glucose levels based on received measurements, memory for storing glucose levels, ports for wired communications, and wireless communication circuits, such as Bluetooth, WiFi, and RF circuits. In addition, dedicated display 104a can determine a historical trend of whether a user's glucose levels are trending down, remaining stable, or increasing. As shown in FIG. 1, dedicated display 104a can present glucose readings over time so a user can easily monitor glucose levels, and can also display an actual value of the current glucose level. In the example of FIG. 1, dedicated display 104a illustrates that the current glucose level is 94 mg/dL.

Display 106a can be any type of display associated with a personal computer, tablet, or smart phone that can execute applications for displaying data relating to glucose levels. As a result, display 106a includes all of the hardware components associated with personal computing devices, including processor(s), memory, wireless connections, a USB port, and others.

Both dedicated display 104a and display 106a can establish alarms to alert a user to glucose conditions. As examples, a user-perceptible alert may trigger when glucose levels are too low (e.g., below 55 mg/dL), at a level defined by the user as low (e.g., a value set between 55 mg/dL and 70 mg/dL), too high, above a level defined by a user, trending down too fast, and trending up too fast. Each display may use the same or different alert values. In addition, alerts can be used to prompt a user to perform a function, such as perform a calibration by entering blood glucose values taken using a separate measurement device. The calibration values can be sent from the display device to the transmitter and used to calibrate glucose data sampled by the continuous glucose sensor system 100.

Alerts can also be sent from the glucose sensor 100 via wireless transmitter to the displays. The alerts can indicate an error with the sensor, a warning that the sensor 103 will expire soon and should be replaced, and an error indicating that a sensor 103 has expired. Another alert that can be sent from the continuous glucose sensor system 100 can indicate that a transmitter battery is low, there is a weak wireless signal between the continuous glucose sensor transmitter 101 and a display, failure in the pairing or authentication process, and other alerts relating to system operation and use. The alerts can be displayed to a user with increasing frequency until one or both of the user acknowledging the alert and the underlying alert condition is resolved.

Display 106a may execute a plurality of applications 108-110 that relate to glucose monitoring, receiving and displaying various types of health information, including exercise activity, controlling and monitoring insulin injections, eating habits, and others. In one embodiment, display 106a receives the same data that continuous glucose sensor system 100 transmits to dedicated display 104a. Display 106a may include a dedicated application 108 created, in one exemplary embodiment, by the manufacturer or an affiliate of the continuous glucose sensor system 100. The dedicated application 108, display 106a, and/or continuous glucose sensor system 100 may be approved medical devices. For example, in one embodiment, continuous glucose sensor system 100, display 106a, and dedicated application 108, alone or in combination, are approved class III medical devices. The dedicated application 108 may control the distribution of medical data received from the continuous glucose sensor system 100 to other applications executing on display 106a to preserve confidentiality and user preferences, as described in more detail below. Although not illustrated, dedicated application 108 and approved third party application 110 may also be connected to and provide information to other applications on display 106a or transmitted to further computing devices and/or server systems.

An approved third-party application 110 may also receive data relating to blood glucose levels. The dedicated application 108 may receive glucose data from continuous glucose sensor system 100, determine what set of data should be provided to an approved third-party application 110, and provide the data to the third-party application 110. A user may configure what types of medical data the dedicated application 108 should provide to the approved third-party application 110. In this manner, the third-party application may receive the same data received by dedicated application 108, a reduced set of data, or encrypted data. While dedicated application 108 has been described as controlling what data is provided to third-party application 110, an operating system executing on display 106a or other software program may also separate the data received from continuous glucose sensor system 100 and provide it, as appropriate, to applications 108, 110.

FIG. 1 also illustrates an additional dedicated display 104b and an additional display 106b. These devices may be additional devices that are within a wireless transmission range from continuous glucose sensor system 100. For example, a user may be at a conference or in a public area where many people have a continuous glucose sensor system 100, dedicated display 104a, and display 106a. Displays 104b, 106b that are connected to another continuous glucose sensor system should not be allowed to connect to continuous glucose sensor system 100. This could cause incorrect data to be displayed from another user and also would constitute a breach of security for medical data. As a result, in one embodiment, each continuous glucose sensor system 100 may limit the number of devices that it connects with, and only connect with paired, authenticated devices in a secure fashion. For example, the continuous glucose sensor system 100 may connect to only a single dedicated display 104a and display 106a at a given time. Limiting the number of devices with which the continuous glucose sensor system 100 can communicate during a particular session also saves battery life of the sensor 100. Additional details including exemplary techniques for limiting the number of devices with which a continuous glucose sensor system 100 can connect at a given time will be provided below with regard to, for example, the embodiments of FIGS. 2, 6-8, 11, 14, and 15.

In addition to limiting the number of devices, the system may also employ security measures to keep medical data private. The security measures can include one-way authentication, two-way authentication, encryption, hashing, and security keys. The encryption employed may be in addition to encryption already offered by wireless standards, such as Bluetooth encryption. One problem that arises is with repeated attempts to attack the security of devices by an unauthorized third-party guessing the security key. To combat this problem, in one embodiment, an application key can be exchanged between continuous glucose sensor system 100, dedicated display 104a, and display 106a, and the application key can change periodically. For example, the application key can change on demand, at predetermined time intervals, in response to a certain event, and in other situations. The term periodically therefore is not limited to defined time intervals but instead relates to periods within which communications are secured using an application key that can change during another communication period.

Figure 2:
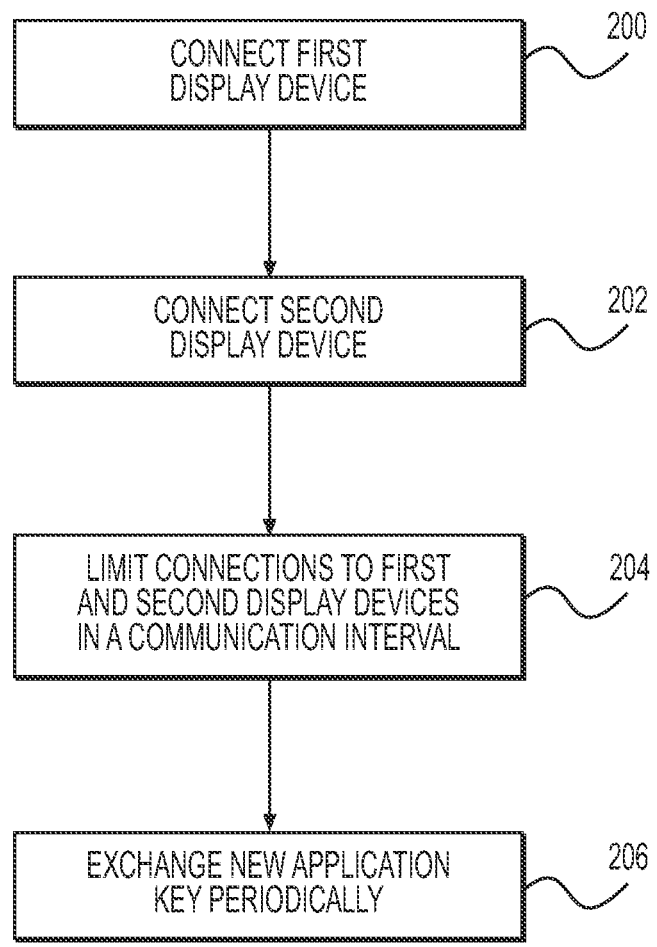
FIG. 2 illustrates an exemplary method for connecting multiple display devices and securing wireless communications.

FIG. 2 is a flow chart of an exemplary method for connecting multiple display devices and securing wireless communications. In the method of FIG. 2, the number of display devices that are connected to a continuous glucose sensor system 100 can be limited to, for example, two display devices. In one embodiment, each display device may be of a different type, such as a dedicated display 104a and a display 106a, although in other embodiments both display devices may be of the same type.

At step 200, the continuous glucose sensor system 100 may connect with the first display device. The connection used may include a variety of different techniques to authenticate and pair the continuous glucose sensor system 100 with the first display device. Exemplary embodiments for authenticating and pairing the continuous glucose sensor system 100 with a display device will be described below.

At step 202, the continuous glucose sensor system 100 may connect with the second display device. As with the connection to the first display device, the connection used may include a variety of different techniques to authenticate and pair the continuous glucose sensor system 100 with the first display device. The type of wireless connection between the continuous glucose sensor system 100 and the first display device need not be the same type of connection as between the continuous glucose sensor system 100 and the second display device. For example, the continuous glucose sensor system 100 may connect with the first display device using a RF connection and with the second display device using a connection, such as a Bluetooth connection.

Next, at step 204, the number of connections may be limited to the first display device and the second display device in a particular communication interval. For example, the continuous glucose sensor system 100 may be limited to connecting with two display devices at a time to conserve battery life and avoid widespread transmission of sensitive medical data. More than two devices may be authenticated for transmission in the situation where a user has, for example, multiple smart phones, a tablet, a laptop, or a personal computer, each of which may act as a display 106a. However, the number of displays that can be connected at a given time may be limited to conserve battery life of the continuous glucose sensor system 100.

In one embodiment, the described methods for authenticating between a continuous glucose sensor system 100 and a display may occur at each communication interval (e.g., every five minutes). The transmitter may inform each display if communications are allowed. Once one device of a given type has been allowed in a communication interval, other devices may be rejected that respond to advertising and have the same device type as the already allowed device.

A variety of different techniques may be used to limit the number of devices. As examples, the continuous glucose sensor system 100 may allow only a single device of given type (e.g., a dedicated display 104a and display 106a). Lists can be stored in memory of the continuous glucose sensor system 100 to track which device types have connected to the continuous glucose sensor system 100, and a combination of hardware level and software level identification and authentication can be used. An exemplary embodiment with additional details of limiting the number of devices will be provided below.

After pairing devices, a user may also enter a prompt through a display to switch to another device. In one embodiment, the user may be actively communicating with the continuous glucose sensor system 100 using a dedicated display and a smart phone and may want to switch to using the dedicated display and a tablet. The user may enter a command through a user interface on any of the smart phone, the dedicated display, or the tablet to request the switch. In response, the continuous glucose sensor system 100 may cease transmissions to the smart phone and begin transmissions with the tablet, after appropriate authentication, pairing, and security measures are in place, as described in detail below.

At step 206, the continuous glucose sensor system 100 may exchange an application key with the connected display devices. Step 206 is an optional step that occurs in some embodiments. Communications may initially be established using a fixed key. The fixed key can be based on a transmitter identifier or a portion of a transmitter identifier printed on the continuous glucose sensor system 100 or transmitter 101. The user may enter the transmitter identifier into the dedicated display 104a and display 106a to establish communications. The transmitter identifier may also be sent from continuous glucose sensor system 100 to the dedicated display 104a and display 106a, so that a comparison can be made between the transmitter identifier received from the continuous glucose sensor system 100 and the transmitter identifier entered by a user. When the transmitter identifiers match, communications may be allowed, or additional security steps may occur to further authenticate the two devices. When the transmitter identifiers do not match, the requested connection may be denied.

Although described as using a transmitter identifier throughout the specification to establish secure communications, the transmitter 101 may also include any other type of identifier stored in memory from the factory. For example, a secure identifier and/or key can be stored in nonvolatile memory prior to initial sale. A user could then download the information needed to perform authentication by their phone, such as a copy of the secure identifier or key, over the internet using the transmitter identifier. An online database may store the decrypting information for each transmitter identifier to provide that information to a user's display during to the pairing process.

As an additional security measure, the continuous glucose sensor system 100 may transmit a separate application key to the connected displays. The application key may remain active for an interval, which may be defined by a period of time, events, or based on other activities or inactivity. An exemplary time interval for using an application key is four hours. Exemplary events include a display going offline or attempting to reconnect. In one embodiment, the dedicated display 104a and display 106a may use the same application key, although in other embodiments each display may use a different application key for secure communications.

Figure 3:
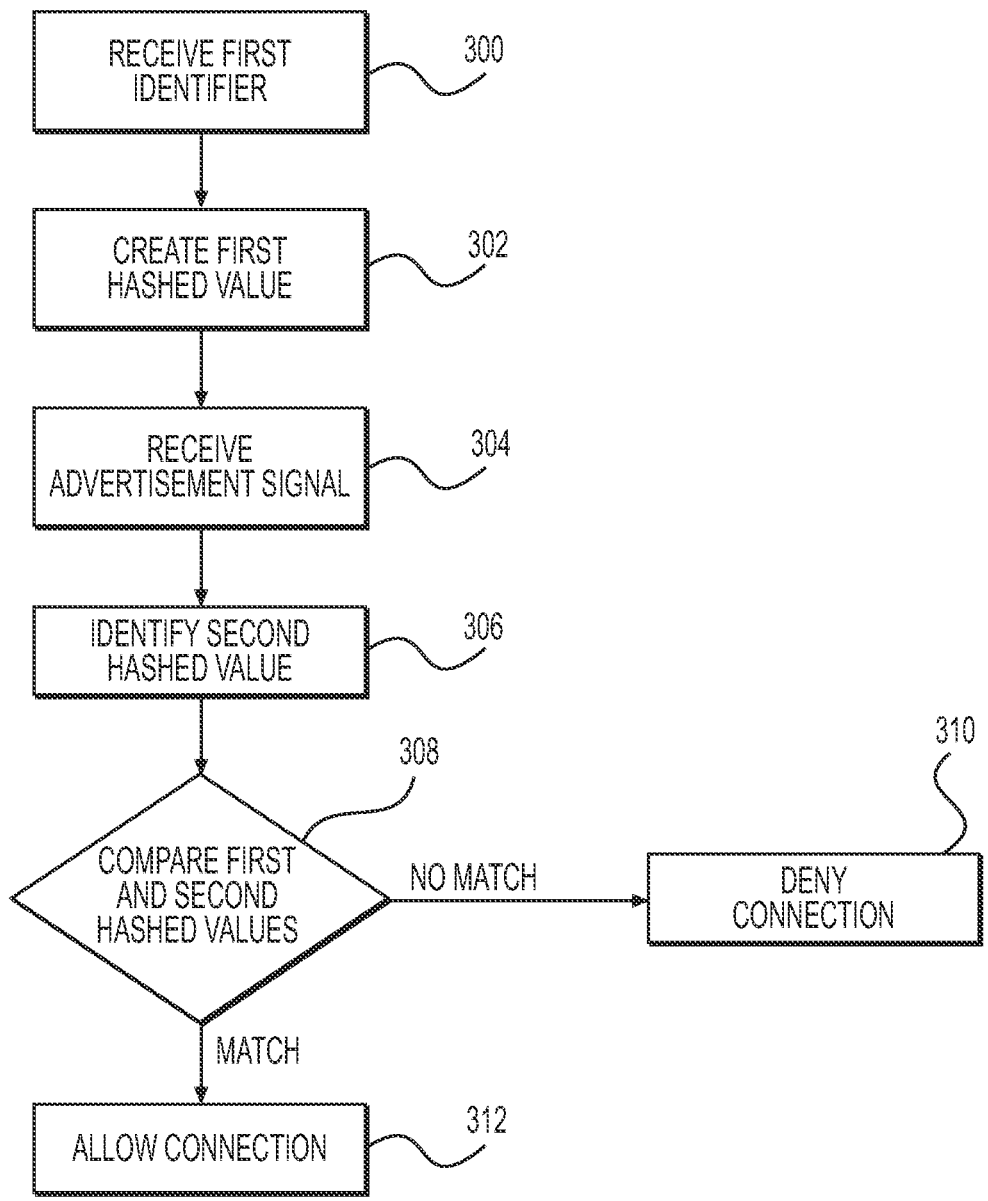
FIG. 3 illustrates an exemplary method for determining whether to allow a connection.

Reference will now turn to FIG. 3, which illustrates an exemplary method for determining whether to allow a connection. The method of FIG. 3 illustrates an exemplary implementation for connecting a display at steps 200 and/or 202 in FIG. 2. In one embodiment, a connection may be allowed when the continuous glucose sensor system 100 and the display have exchanged identifying information. In the example of FIG. 3, the identifying information may include a transmitter identifier that is printed on the back of the continuous glucose sensor system 100 or transmitter 101. However, transmitting the transmitter identifier itself can lead to a security breach by unauthorized devices nearby that can listen or sniff for transmissions. The unauthorized devices can listen for transmissions from the continuous glucose sensor system 100, obtain the transmitter identifier, and then enter the same value on another display in an effort to circumvent security. The method of FIG. 3 therefore adds an additional layer of security by using a hashing algorithm on the transmitter identifier so that unauthorized displays cannot pretend to be an authorized display by listening for the transmitter identifier.

At step 300, a display may receive a first identifier. For example, a user may look on the back of a continuous glucose sensor system 100 and find a transmitter identifier printed on the back of the sensor system 100 or transmitter 101. The display may prompt a user to enter the transmitter identifier to begin the process of establishing a connection.

At step 302, the display may create a first hashed value from the first transmitter identifier. Any type of hash function may be used to create a hashed value. A hashing function is used to map data of a given length into a different length. As an example, a nine digit transmitter identifier may be entered by a user. The hashed value may include the last four digits of the transmitter value. In other embodiments, the hashed value may be a translation of any of the digits, so that a combination such as 123456789 becomes ABF after executing the hashing algorithm. It will be appreciated that a wide variety of hashing algorithms exist and can be used to translate data into a different form.

A display may receive an advertisement signal from the continuous glucose sensor system 100 at step 304. An advertisement signal is a signal used in the pairing process where a device transmits a message advertising its availability for a connection. In one embodiment, the advertising period may last for a defined time interval, such as seven seconds, and may repeat for up to a defined number of iterations in a given communication interval. For example, two advertising periods of seven seconds each may be used at five minute communication intervals. The advertising periods may also have different durations based on the type of device, such as four seconds to pair displays and two seconds to pair a dedicated display 104a.

The user may place their display into an advertising mode that causes the display to scan for any advertising signals. This process may occur, for example, when a user inserts the transmitter into the continuous glucose sensor system 100 upon initial startup, or when a user wants to add a new display to the system. The transmitter 101 on the continuous glucose sensor system 100 may broadcast an advertisement signal that includes a hashed version of the transmitter identifier. In this embodiment, the transmitter identifier that is printed on the back of the continuous glucose sensor system 100 or transmitter 101 may also be stored in memory within the continuous glucose sensor. The hashing algorithm may also be stored in memory by the continuous glucose sensor system 100, so that it can create a hashed value from the stored transmitter identifier and send the hashed value to the display in the advertisement signal.

After the initial connection between the continuous glucose sensor system 100 and a display, the display may enter a state where it searches for advertisement signals automatically. In one embodiment, each communication interval by the transmitter involves the process of receiving advertising signals and performing authentication. The display may automatically enter a state to search for advertising signals by knowing that the transmitter will wake up and transmit advertising signals periodically. Therefore, the display need not continuously search for advertising signals, allowing the display to conserve battery life. In other embodiments, however, the display may remain in a state of constantly monitoring for advertising signals by their dedicated display 104a or other display 106a, such as a smartphone.

At step 306, the display will parse at least one of the advertisement signal or signals associated with the advertisement signal to identify the second hashed value. The second hashed value may be, in one embodiment, the result of executing the hashing algorithm on the transmitter identifier stored in memory by the continuous glucose sensor system 100. The second hashed value may be sent in the advertisement signal itself. The advertising signal may include a payload with a short name, flags, a unique user identifier, and manufacturing data. The short name and unique user identifier, which may be, for example, 128 bits, may identify the transmitter. The manufacturing data field may contain the transmitter hashed value used for the authentication phase. In another embodiment, the second hashed valued may be sent in signals associated with the advertisement signal. For example, after receiving an advertisement signal and allowing a connection, the second hashed value may be sent either automatically or in response to a request.

The hashing algorithm can be either one-way, meaning the original value cannot be obtained from the hashed value, or two-way, meaning the hashed value can be returned to the original transmitter identifier. In addition, hashing may include an AES 128 bit encryption with Electronic CodeBook mode, another form of encryption, cryptography, and other techniques to transform the transmitter identifier into a hashed value. As a result, in one embodiment, the transmitter identifier is not transmitted in an advertising signal from the continuous glucose sensor. Instead, a hashed value can be sent. An unauthorized display that receives this hashed value cannot recreate the original transmitter identifier, and therefore cannot improperly enter the transmitter identifier into another display to gain unauthorized access. As an example, a sixteen byte key may be created by repeating the first four bytes of the transmitter identifier four times in sequence. The key may optionally be provided to an AES 128 bit algorithm using Electronic CodeBook mode. Both the continuous glucose sensor system 100 and the display may compute the key.

Next, the display may compare the first and second hashed values. In one embodiment, the hashing algorithms may be designed so that a perfect match of the same characters results in a match. Continuing with the example above, the display may create a key and compare it to the hashed value received in the advertising signal. In other embodiments, a match occurs even in the absence of the same characters being present in the first hashed value and the second hashed value. For example, if the first hashed value and the second hashed value differ by a predetermined amount, then a match can be found. The first hashed value could be 123, and the second hashed value could be 456. Although the two do not match in the sense of being the same series of characters, the hashing algorithm can know that the first numerical entry in the second hashed value should be one greater than then last numerical entry in the first hashed value. Many other examples are also possible.

The second hashed value also may be a key needed to reverse a hashing algorithm. Instead of transmitting a hashed value of the transmitter identifier, the second hashed value may be a key needed by the authenticating device to reverse or decrypt an encrypted transmitter identifier. A match can be found when the second hashed value can be used as a key to obtain the transmitter identifier. It will therefore be appreciated that the hashing algorithm executing on the display and the hashing algorithm executing on the continuous glucose sensor system 100 need not be the same algorithms or create the same series of characters. Instead, the first and second hashing algorithms can be designed to create first and second hashed values that have a defined relationship that will result in a match.

In the situation where a match is not found, the connection may be denied at step 310. However, where a match is found, the connection may be allowed at step 312. In one embodiment, executing the method of FIG. 3 may result in communications between the continuous glucose sensor system 100 and a display. However, executing step 312 to allow a connection also includes embodiments where the process of fully pairing the devices can continue on to further steps. That is, the result of step 312 can be a connection in the form of, for example, an unsecured connection. Additional steps may make the connection secure.

For example, in addition to hashing a transmitter identifier, a whitelist including allowed devices may be accessed, an application key may be exchanged, encryption can be used, and additional steps may be included before communications can be exchanged between the continuous glucose sensor system 100 and a display. These additional steps are described in the subsequent embodiments (e.g., FIGS. 4-8, and 13-15) and may be used instead of, or in addition to, the exemplary method in FIG. 3. In one embodiment, after step 312, a message may be displayed to a user that the continuous glucose sensor system 100 has been paired to a display alone or along with a message indicating that further authentication may occur.

The method of FIG. 3 therefore allows a hashed value to be exchanged between the continuous glucose sensor system 100 and display for use in an authentication process. Hashed values can vary based on the particular display that is requesting a connection. For example, as described below, the type of each display can also be known and identified in the system. The continuous glucose sensor system 100 may use a first hashing algorithm for a first type of display, and a second hashing algorithm for a second type of display.

Figure 4:
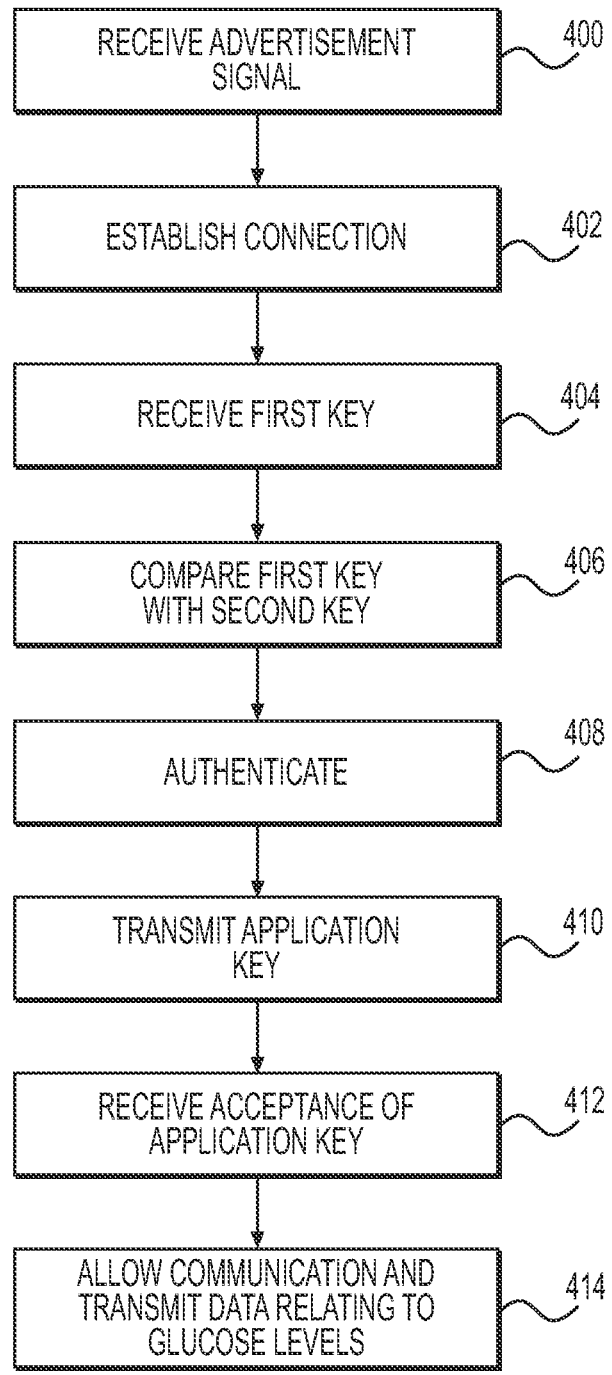
FIG. 4 illustrates an exemplary method for authenticating and establishing communications between a continuous glucose sensor and multiple displays.

FIG. 4 illustrates an exemplary method for authenticating and establishing communications between a continuous glucose sensor and multiple displays, which may be part of steps 200 and 202 in FIG. 2. The embodiment in FIG. 4 exchanges an application key to provide an additional level of security before transmitting data relating to glucose levels from the continuous glucose sensor to the displays. An application key may be created by software and updated periodically as described below.

At step 400, a display may receive an advertisement signal from the continuous glucose sensor system 100 and then establish a connection at step 402. The process of establishing a connection may also involve comparing identifying information, such as a type of a device, to a whitelist stored in memory, as described in more detail below in, for example, FIGS. 6, 7, and 13-15. In this example, Bluetooth communications can provide the advertising signal and step of establishing a connection.

Next, at steps 404 and 406, the first key may be received and compared with a second key. As with reference to FIG. 3, the first key may be a hashed version of a transmitter identifier, a key used to decrypt a transmitter identifier, or other information associated with encrypting and decrypting a transmitter identifier to avoid inappropriate misuse by an unauthorized device. The first key may be received at step 404 in response to a request sent from the display to the continuous glucose sensor system 100 upon establishing a connection. In other embodiments, the display may receive the first key automatically upon establishing a connection or in advertising signals.

The process of checking for a match between the first hashed value and the second hashed value can occur on the continuous glucose sensor or the display. After the advertisement period and establishing a connection, the first key may be sent in response to a request including a challenge value. The challenge value may be used to encrypt the transmitter identifier or executing a hashing algorithm on the transmitter identifier to create the first key.

At step 406, the first key may be compared to a second key. As described previously, a match may be found in a variety of circumstances where a predefined relationship is found to exist between the first key and the second key. If the comparison results in a match between the first and second key, the continuous glucose sensor system 100 and the display may be authenticated at step 408.

Next, at step 410, an application key may be exchanged between the continuous glucose sensor system 100 and the displays. In the embodiment of FIG. 4, beyond exchanging a key between the continuous glucose sensor system 100 and display, an application key may also be used to provide secure communications. In one embodiment, the transmitter identifier may be printed on the back of a transmitter 101. As a result, an unauthorized user may view the transmitter identifier and use that information to improperly authenticate their display. In addition, because the transmitter identifier may, in one embodiment, remain the same, users who try to sniff communications have additional opportunities over time to attempt to circumvent hashing or encryption of the transmitter identifier. Adding an additional application key provides additional security and the ability to periodically change the key to ensure continued secure communications.

The application key may be sent either from the continuous glucose sensor system 100 to the display, or from the display to the continuous glucose sensor system 100. The device receiving the application key may provide an acknowledgment that it has accepted the application key at step 412. In some embodiments, the receiving device may not acknowledge the application key due to an error in the communication. For example, in the embodiment where a display sends the application key to a transmitter, the display may be out of wireless range from the transmitter 101. As another example, the transmitter 101 may have received the application key and transmitted an acknowledgment back to the display, but the display may not have received the acknowledgment. In the example where an acknowledgment is not received, the display can operate according to several optional embodiments.

In one option, the display may discontinue communications and attempt to resend the application key. In this embodiment, steps 410 and 412 may repeat until successful acknowledgment of the application key is received. In another embodiment, the display may switch to using the application key even without receiving the acknowledgment. If communications succeed and the display receives responses to commands based on the application key, the display may continue with using the application key despite not receiving an acknowledgment. The display instead has confirmed receipt of the application key through the subsequent successful communications, indicating the response acknowledgement message was dropped or experienced a communication error. Another option for handling the situation where an acknowledgment is not received is to continue using any prior application key. The display in this embodiment may maintain both application keys—the prior key and the key that was not acknowledged—until an acknowledgment is received or a new communication interval begins. In addition, the display may repeat step 410 by sending the application key again until acknowledgement is received.

Once acknowledgment has been received, communications between the continuous glucose sensor system 100 and the display may be allowed and data relating to glucose levels may be transmitted from the continuous glucose sensor system 100 to the display. The process in FIG. 4 may repeat for each display that connects with the continuous glucose sensor system 100. The connection process may proceed concurrently between the continuous glucose sensor system 100 and a plurality of displays or in sequence. In addition, the application key need not be the same for each display. In one embodiment, each pair of display and continuous glucose sensor system 100 may use different application keys.

Figure 5:
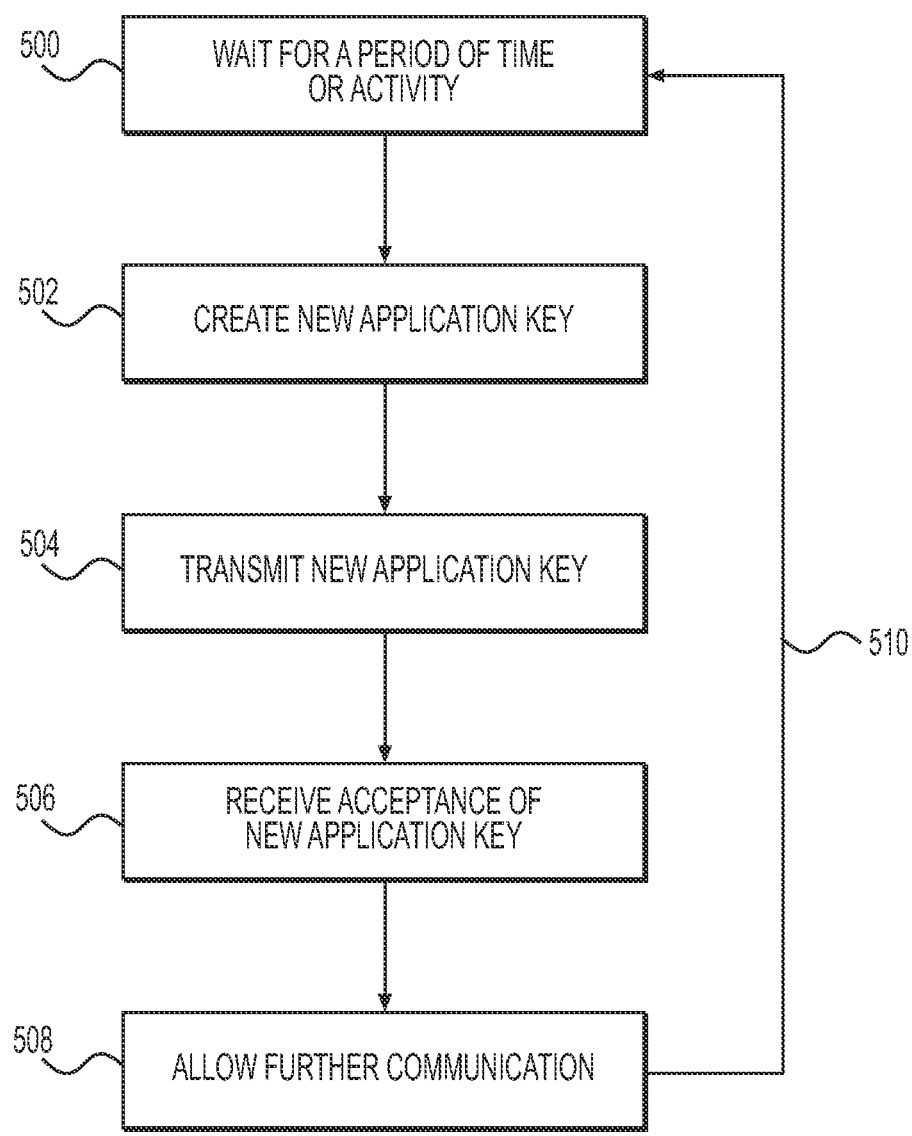
FIG. 5 illustrates an exemplary method for updating an application key.

Reference will now turn to FIG. 5, which illustrates an exemplary method for updating an application key. The method illustrated in FIG. 5 may be used in addition to the method of FIG. 4, as well as in other embodiments. By updating the application key periodically, security can be enhanced and repeated attempts to access transmission of secure medical data can be defeated.

At step 500, the continuous glucose sensor system 100 and display may wait for a period of time or until an activity occurs. During the period of waiting, the current application key may be used to secure communications between the continuous glucose sensor system 100 and the display. The process of switching to a new application key may occur at defined time intervals, such as hourly, or when a particular activity occurs. Examples of activities that can trigger exchange of a new application key include a display going offline and then coming back online (e.g., a display losing its network connection with the continuous glucose sensor system 100 and then reestablishing a connection), a user switching to a new display, rejection of an attempt by another display to connect with the continuous glucose sensor system 100, and others.

At step 502, the display or continuous glucose sensor system 100 may create a new application key. In the embodiment of the display transmitting the new application key to the continuous glucose sensor system 100, the display may create the new application key. The key may be created prior to step 500, during the waiting period, or upon detecting the period of time or activity in step 500.

The new application key may be transmitted to the receiving device at step 504. For example, the display may transmit the new application key to the continuous glucose sensor system 100. Next, an acknowledgment indicating the new application key was accepted may be received at step 506. As with the embodiment of FIG. 4, various techniques may be employed for handling the situation where an acknowledgment of the new application key is not received. The techniques described with reference to FIG. 4 therefore apply equally to switching to a new application key.

Once acceptance has been received, further communications can occur at step 508. In one embodiment, as described previously, further communications may occur even without receiving an acknowledgment by continuing to use the prior key. This allows seamless operation for a user while the process of FIG. 5 repeats to successfully update the application key. FIG. 5 may repeat at step 510, for example, at predetermined time intervals, upon detection of an activity, and when successful acknowledgment of the new key is not received.

Figure 6:
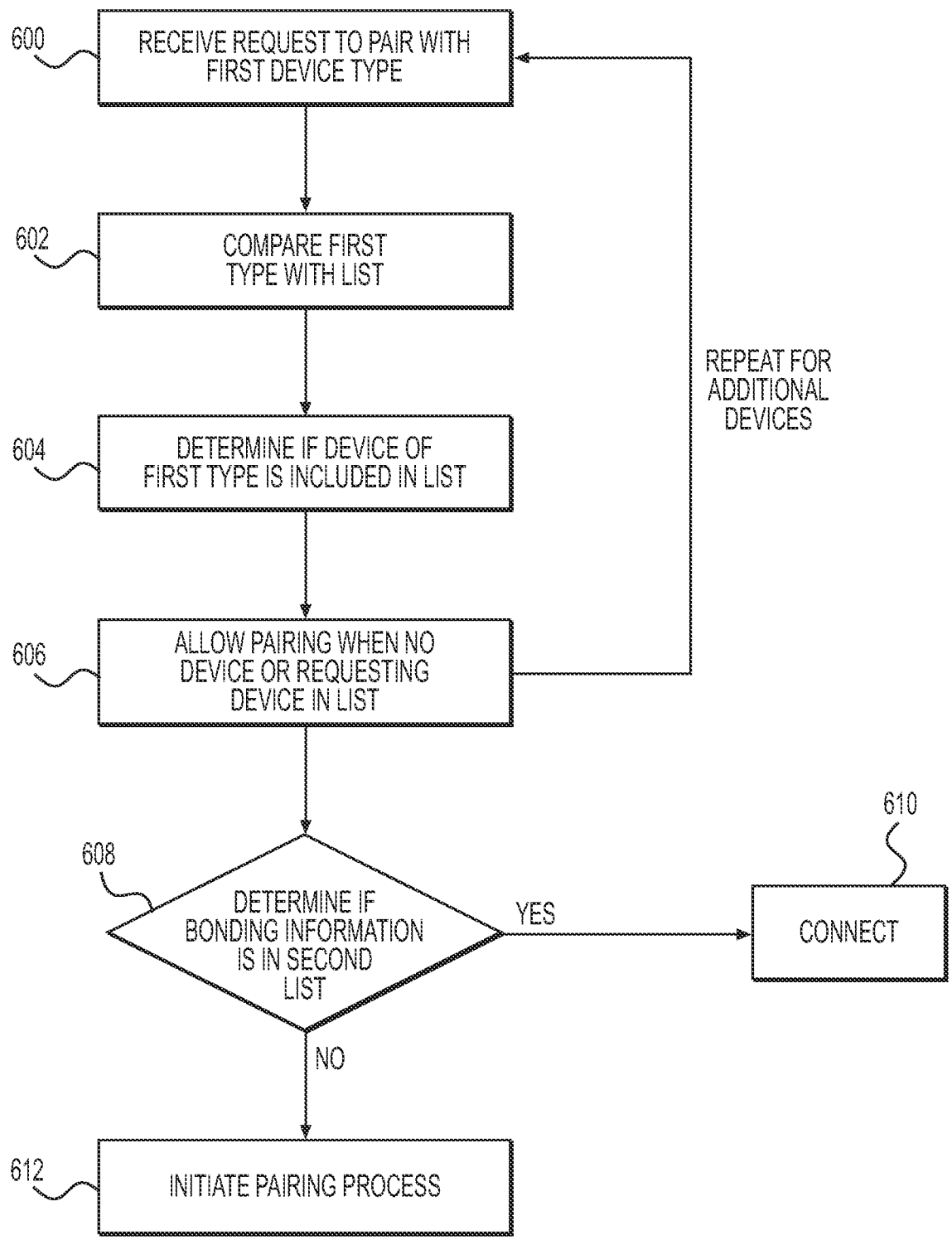
FIG. 6 illustrates an exemplary method for connecting a continuous glucose monitor to one or more displays based on a device type.

Another issue that arises relates both to conserving battery life and limiting the number of display devices that can connect to the continuous glucose sensor system 100 at a given time. Having too many devices connected at once places increased burdens on the battery lift of the continuous glucose sensor 100 as it must communicate with many devices, which reduces the periods in which the continuous glucose sensor 100 can enter a low-power sleep state. FIG. 6 illustrates an exemplary method for connecting a continuous glucose sensor to one or more displays based on a device type. FIG. 6 is one example of limiting connections, as described with reference to step 204 in FIG. 2.

The continuous glucose sensor system 100 can be a small device worn on the body of a user that is powered by a battery. As a result, conserving battery life may be an important consideration for providing a system that can continuously monitor glucose levels. Each data transmission between a continuous glucose sensor system 100 and a display consumes battery life. To conserve battery life, the transmitter 101 on the continuous glucose sensor system 100 may be placed in a sleep state and brought into an active state periodically, such as on a time interval of every five minutes. In addition, the continuous glucose sensor system 100 itself may be placed in a sleep state and periodically activated. As an additional measure to conserve battery life, in one embodiment, the number of displays with which the continuous glucose sensor system 100 exchanges data and commands can be limited. FIG. 6 illustrates an exemplary method for limiting the number of devices that connect to a continuous glucose sensor system 100 based on a type of device.

At step 600, the continuous glucose sensor may receive a request to pair with a first device type. For example, the dedicated display 104a may request a connection with the continuous glucose sensor system 100. In one embodiment, the request may come as part of an advertising and connect process as previously described. The request may include an indication of the type of device that seeks a connection with the continuous glucose sensor system 100. The device type may be included in the message, or the device type may be determined by the continuous glucose sensor system 100 based on other information included in or associated with the request. For example, a device type identifier may be used to determine the device type, or a user may provide an input to the display indicating the type of device, such as a tablet, personal computer, or smart phone.

The continuous glucose sensor may store a first list of devices and their associated device types in memory. The first list may initially be empty, and as new devices are paired, authenticated, and connected, the device may be added to the first list in memory. The first list can be a white list, which is a hardware level list allowed device types. Devices having an unrecognized device type may be denied requests for connections. Upon receiving a request indicating the first type of device requesting a connection, the continuous glucose sensor system 100 may compare the first type of device with the first list stored in memory at step 602. The continuous glucose sensor system 100 may determine if a device having the first type is already included in the first list at 604. If the device having a given device type (e.g., dedicated display or other display) is not on the first list, and the device type is recognized, that device may be added to the first list at step 606 to allow pairing. If the device is already on the first list, then the method may continue on to step 608.

If another device having the requesting device type is already included in the first list, the continuous glucose sensor system 100 may determine if a maximum number of devices having that device type are already included in the first list. For example, the first list may allow for a certain number of entries of each device having a given type, such as one device, two devices, five devices, or any other number based on the size of memory and other system considerations. The process in steps 600-606 may repeat for additional devices seeking a connection with the continuous glucose sensor system 100. In one embodiment, a single dedicated display 104a and a single display 106a of another type may be connected to the continuous glucose sensor system 100.

In addition, the advertising period may vary based on the number of devices in the first list. In one embodiment, a single advertisement period may be used if the first list is empty and no displays have authenticated. If a display responds during the advertising period, but the connection is rejected, the advertising period can continue for its remaining duration. In the example where at least one display is already included in the first list, two advertising periods can be used. If a display is rejected and the advertising period in which the display was rejected still has time left, the continuous glucose sensor system 100 can continue to advertise for the remaining period of time. Optionally, where one display is included in the first list, the second advertising period may not use a comparison to determine if the requesting device type is included in the first list. In the embodiment where the first list is full, such as where the first list includes a device of a device type as a dedicated display and a device of the device type as another display, the filter using the first list can be active during two advertising periods.

At step 608, the continuous glucose sensor system 100 may proceed with determining if bonding information is included in a second list. While the first list contains a list of devices that can proceed with the advertising and pairing process, the second list may be, in one embodiment, a software-level list that contains the bonding information resulting from a successful pairing between the continuous glucose sensor system 100 and a display. The first list and the second list may be stored in non-volatile memory. As a result, if the display requesting a connection has previously paired and connected with the continuous glucose sensor system 100, its bonding information can be stored by the continuous glucose sensor system 100 in a second list. By storing bonding information, the next time a device requests a connection the connection process can proceed without delay.

The bonding information may include, in one embodiment, information used to establish a connection. In addition, the bonding information may include additional authentication information, such as a transmitter identifier, hashed transmitter identifier, encryption or decryption keys, the current application key, and a prior application key. If the bonding information is already included in the second list for the device requesting a connection, the connection may be established at 610, allowing transmission of commands from the display to the continuous glucose sensor system 100 and data relating to glucose values from the continuous glucose sensor to the display.

If, however, the bonding information for a display requesting a connection is not included in the second list, the pairing process may proceed to include the steps required to establish the given type of connection. For example, a pairing process can occur at step 612, which can include any of the previously described embodiments.

Figure 7:
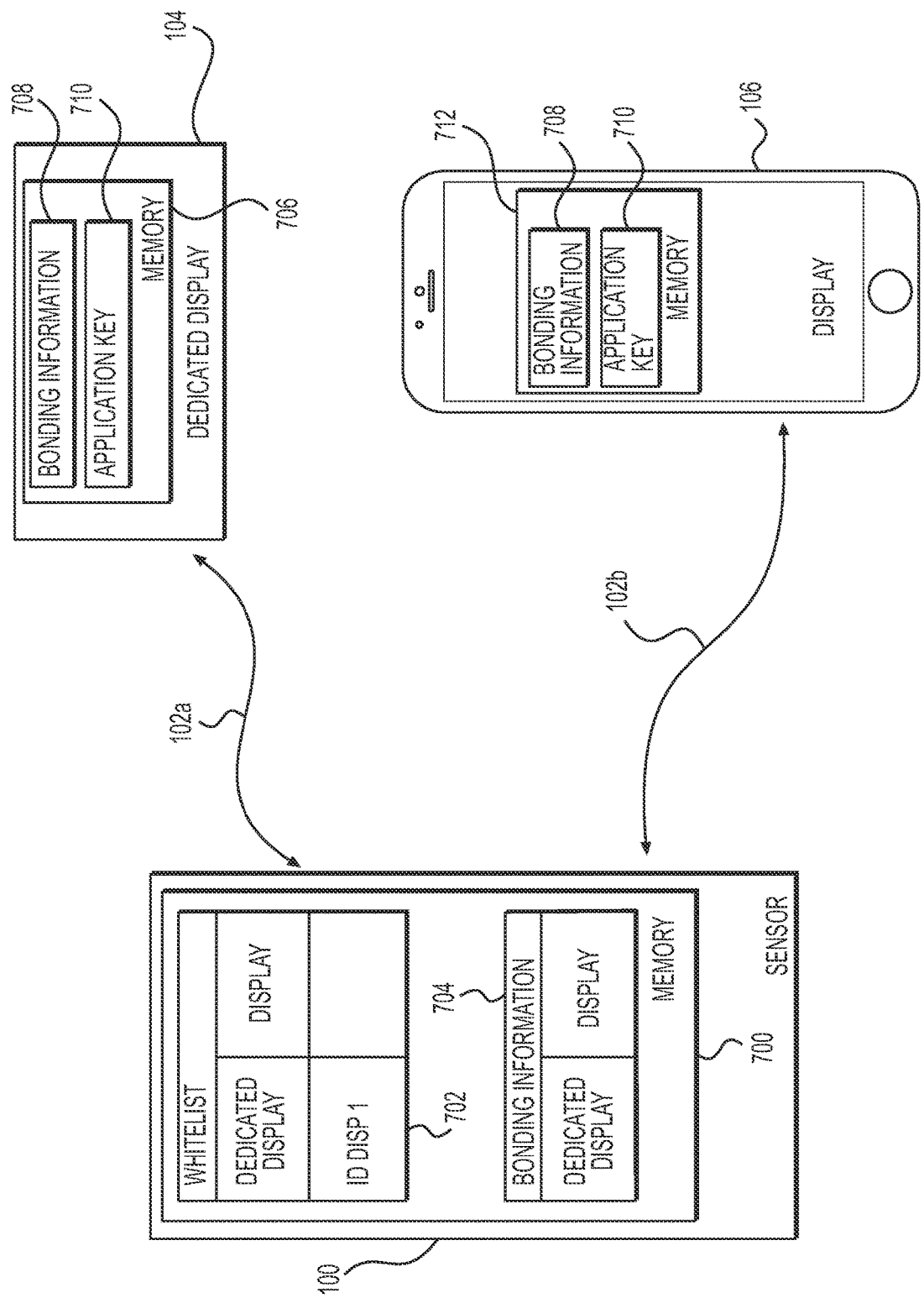
FIG. 7 illustrates an exemplary system diagram of storing connection information.

FIG. 7 illustrates an exemplary system diagram of storing connection information. As described with reference to FIG. 1, a continuous glucose sensor system 100 may wirelessly connect with a dedicated display 104 and display 106. The continuous glucose sensor system 100 may include memory 700 for storing various information used to implement the disclosed embodiments. A whitelist 702, also referred to in some embodiments as a first list, may include a list of devices types that are allowed to connect with the continuous glucose sensor system 100.

As illustrated, the list may include two columns for each type of device, one column for dedicated displays 104a and another for other displays 106a. In other embodiments, additional columns may be included and the device types may be further refined. For example, instead of a category for devices having a type of a display, each specific type of display may be separately stored, such as a tablet, personal computer, laptop, or smart phone. In addition, while described as a first list and illustrated as a table, it will be appreciated that the allowed device types may be stored in a variety of other fashions, including a database. In the example shown in FIG. 7, whitelist 702 has previously registered a dedicated display having a device identifier ID DISP1.

Continuous glucose sensor system 100 may also store bonding information in a separate table 704 in memory 700. The bonding information may include, for example, information used to pair and authenticate a display for communication with the continuous glucose sensor system 100. Bonding information may be stored for the displays that connect with the continuous glucose sensor system 100 and may be maintained in memory persistently for future reconnections.

In one embodiment, dedicated display 104 may also include memory 706 for storing bonding information 708 and, for example, an application key 710. The stored application key may include both the current application key and a previous application key. Likewise, display 106 can include memory 712 with bonding information 708 and any application keys 710.

Figure 8:
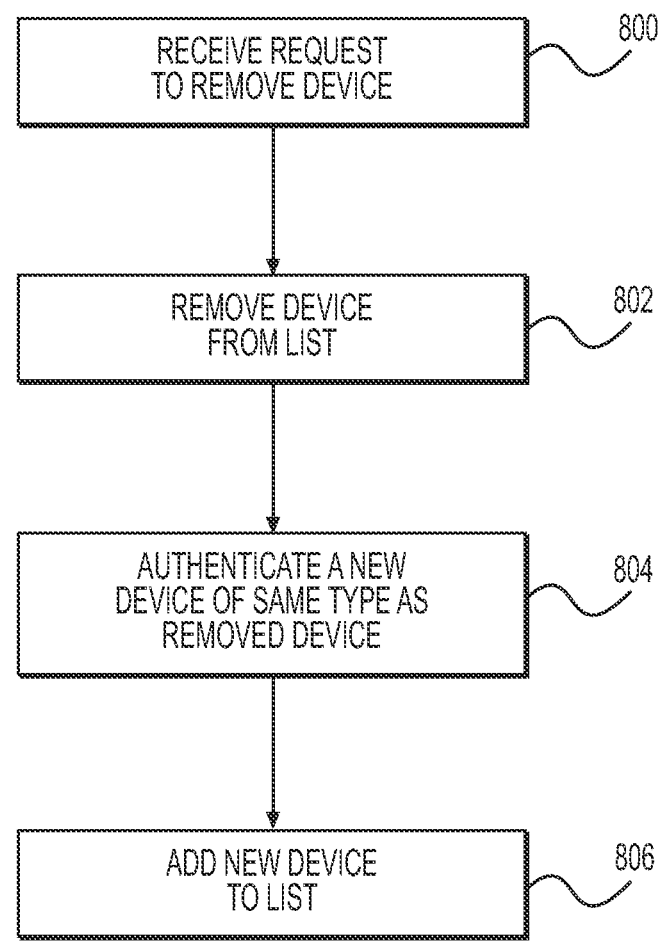
FIG. 8 illustrates an exemplary method for removing displays from authorized lists of displays.

FIG. 8 illustrates an exemplary method for removing displays from authorized lists of displays. After devices have been added to the whitelist and bonding information has been stored, a user may also want to remove a device from the whitelist or remove bonding information. For example, a user may want to wipe clean all devices from memory or remove a single device when the user has replaced their smart phone. In addition, there is a problem that a user might lose or break a display device and not be able to remove the display device from the list of authorized displays. The method of FIG. 8 provides an example of a way in which old display devices can be periodically removed from the whitelist when they have not recently communicated with the transmitter 101, which can indicate that a user no longer uses that display device.

At step 800, the system may receive a request to remove a device from the list of authorized displays. For example, a user may use their current smart phone to indicate that they want to remove that smart phone prior to adding a new display. The request may be entered through a user interface on the display, and transmitted to the continuous glucose sensor system 100. The continuous glucose sensor system 100 receives the request to remove the device from its list of authorized displays. In other embodiments, a user may provide an input to remove a display from a device other than the display being removed. For example, the continuous glucose sensor system 100 may provide a list of authorized devices to the dedicated display. The user could then provide a command from the dedicated display to remove a different display, such as a smart phone. In this manner, the dedicated display can be used to remove and replace a lost smart phone or other display. Similarly, another display could be used to provide a command to remove and replace a dedicated display, allowing replacement of the dedicated display when it is lost or malfunctioning.

Step 800 may also be performed automatically without any request from a user. In one embodiment, a display may be removed from the list if it has not connected to the continuous glucose sensor system 100 for a given period of time and/or connection intervals. As an example, a display that has not connected to the continuous glucose sensor in the past 15 minutes, 30 minutes, hour, day or two weeks may be removed from the first list. As another example, a display that has not connected to the continuous glucose sensor in the prior given number of communication intervals, such as two, three or four may be removed from the first list. Note that in some embodiments, the prior bonding information can be retained in the second list, however, to facilitate quick reconnection at a later time, without needing user input. The process of automatically removing displays that have not connected in a period of time may be used concurrently with allowing a user to request removal of a device discussed above.

At step 802, the continuous glucose sensor system 100 may remove the device from its first list. In one embodiment, the display to be removed can be removed from the whitelist. Alternatively or additionally, the display may also be removed from the second list containing bonding information. In one embodiment, however, a display may be removed from the whitelist but its bonding information may be maintained in the second list to facilitate reconnecting the removed display at a later time. The device may store up to a certain number of display devices, such as five, with devices having recent communications being placed at the top of the list and devices having older communications or having ceased communications being placed at the bottom of the list. As a new device needs to be added to the list (described below), an old device that has not had recent communications relative to the other devices on the list can be removed to create a space for the new device. The continuous glucose sensor system 100 may also transmit a message to the dedicated display and display to indicate that a particular device should be removed from the list of authorized devices.

Next, at step 804, a new device may be authenticated that has the same device type as the removed device. Of course, in previously described embodiments, devices of a different type may be added at any time up to a maximum number of devices of the different type. However, if the whitelist is full and no more devices of a given type can be stored, a user may want to remove an old device from the list and replace it with a new device having the same type. One example is a user upgrading their tablet and replacing with a new device. The request may come from, for example, the new device and may trigger the previously described authentication and pairing processes.

At step 806, the new device may be added to the whitelist using the techniques previously described. In addition, the new device may complete the authentication and pairing process so that bonding information can be stored in the second list.

Figure 9:
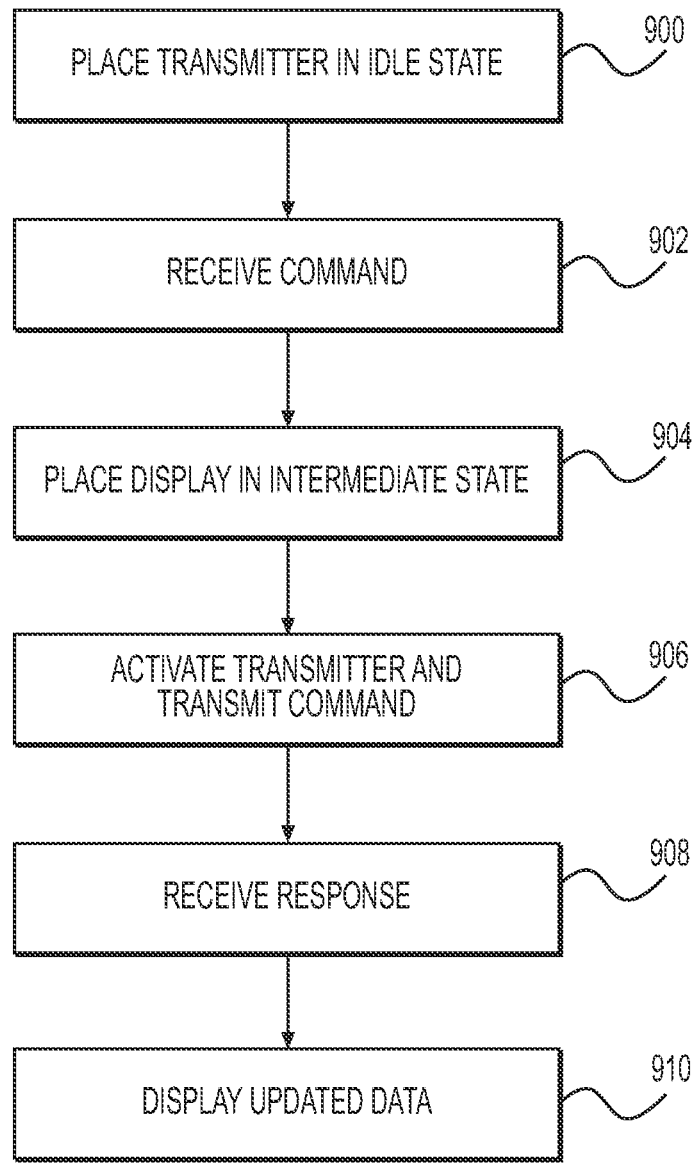
FIG. 9 illustrates an exemplary method for updating data in response to a command.

FIG. 9 illustrates an exemplary method for updating data in response to a command. A system with a continuous glucose sensor system 100 that transmits data to multiple displays may cause synchronization challenges associated with presenting data relating to glucose levels. A user expects to see the same glucose levels displayed on each of the dedicated display 104a and the display 106a since both displays derive their data from the same continuous glucose sensor system 100. However, each display can also provide commands to the continuous glucose sensor system 100 that can change the glucose data. For example, either display may send a command to start a sensor 103 when a user has replaced their sensor 103. In one embodiment, a command to start a sensor 103 can cause the continuous glucose sensor to enter a warm-up phase during which calibration levels are entered to ensure accuracy. As another example, either display may transmit a command to the continuous glucose sensor system 100 to stop a sensor 103 before removing it or when the sensor 103 needs to be taken offline. Another example includes sending a calibration command from a display to the continuous glucose sensor system 100.

Figure 10B:
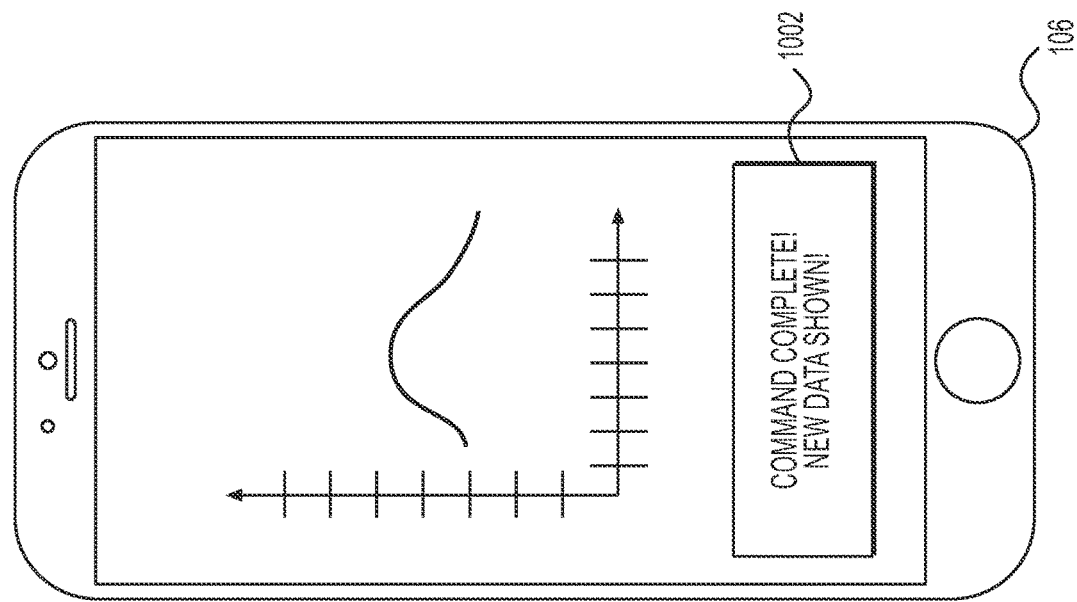
FIGS. 10A and 10B illustrate exemplary user interfaces for processing a command.
Figure 10A:
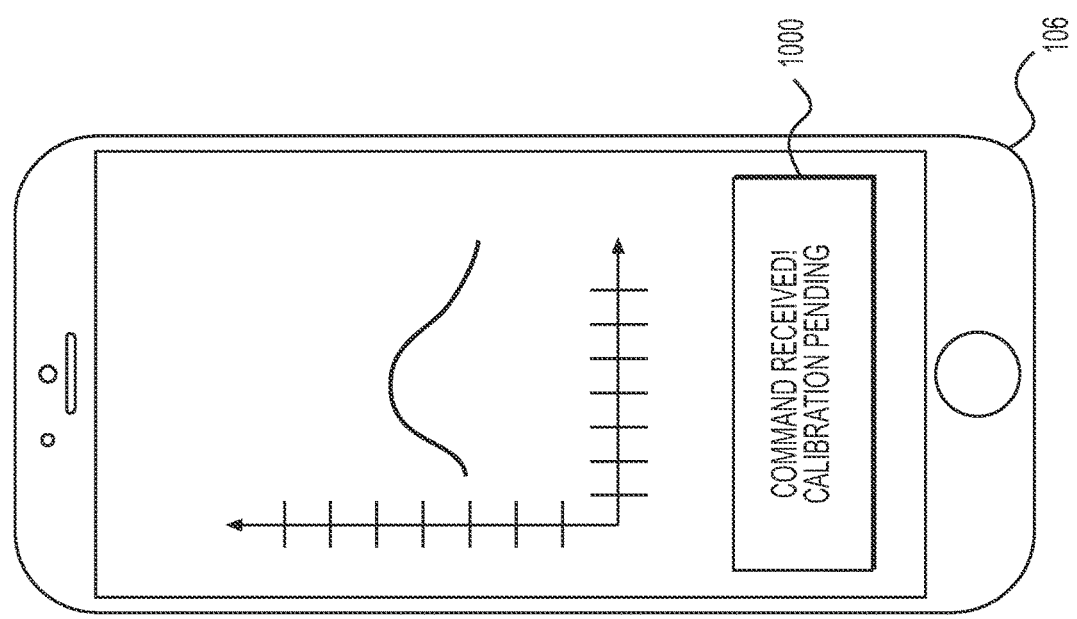
Figure 11:
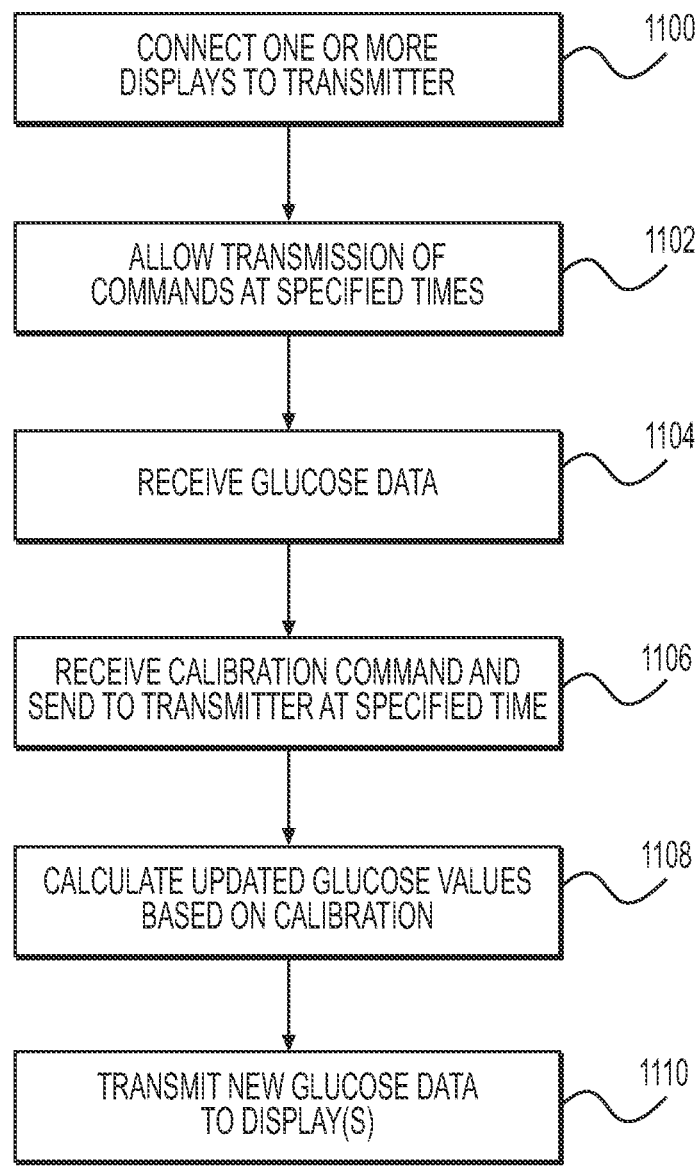
FIG. 11 illustrates an exemplary method for updating multiple displays in response to a command.

Because, in some embodiments, the transmitter 101 on a continuous glucose sensor system 100 may be active intermittently, such as every five minutes, the command may not be immediately received by the continuous glucose sensor system 100. The user expects to receive an indication that the command has received immediately. In addition, when the continuous glucose sensor system 100 enters an active state, it may process commands from the display that did not send the command first. As a result, the display that did not send a command may receive glucose values from the last five minutes, but then the second display may send a command to stop the continuous glucose sensor system 100 or use new calibration values. Once that command has been processed, the second display will show the new glucose values based on the new calibration or will display a different sensor state, such as offline, even while the other display continues to show an outdated glucose level or sensor status. This can cause one display to show outdated data compared to a display that sent a command until the next period when the continuous glucose sensor becomes active and sends the updated glucose levels or sensor status to both displays. FIGS. 9-11 illustrate exemplary embodiments for updating both displays in response to commands.

At step 900, the transmitter 101 on a continuous glucose sensor system 100 may enter an idle state. The idle state may last for five minutes in one embodiment. During the idle time, a display may receive a command at step 902. Commands may be placed in a queue and sent to the continuous glucose sensor system 100 in a batch transfer when it resumes an active state. However, the display may be placed in an intermediate state in the meantime to provide confirmation to a user that the command has been received. For example, a user may enter a command to stop a sensor 103. Because the command may not be sent while the transmitter for the continuous glucose sensor system 100 is in an idle state, the display may continue to show an active status for the sensor 103 even after the command to stop the sensor 103 has been entered by a user.

The display may therefore be placed in an intermediate state at step 904, such as by displaying an indication that the command has been received and is being processed. In addition, the display may illustrate an exemplary time at which the command will be complete based on the time remaining until when the transmitter will resume an active state. FIG. 10A illustrates an exemplary user interface in an intermediate state. As shown at 1000, a message may be displayed that a command was received and calibration is pending. In this example, the command may request recalibration, although a variety of other commands can also be used.

During the intermediate state before a new glucose value has been received from the continuous glucose sensor system 100 based on the new calibration, the display 106a and/or dedicated display 104a may also display a new glucose value based on the estimated new calibration. Once precise calibration has been completed with the continuous glucose sensor system 100, the updated values received from the transmitter 101 may be used in place of the estimated values. While estimated values are displayed, the user may receive, as part of the intermediate state notification, an indication that estimated values are being displayed and optionally that the estimated values will be updated when calibration completes.

At step 906, the transmitter 101 on the continuous glucose sensor system 100 may activate and the command may be sent from the display to the continuous glucose sensor system 100. The continuous glucose sensor system 100 may process the command and send a response back to the display that sent the command at step 908. Next, at step 910, the display may be removed from the intermediate state and the updated data may be displayed. For example, as shown in FIG. 10B, a message 1002 can be displayed indicating the command is complete and new data is shown.

FIG. 11 illustrates an exemplary method for updating multiple displays in response to a command. At step 1100, one or more displays may connect to a transmitter on a continuous glucose sensor system 100 as previously described. At specified times, such as periodically when the transmitter 101 enters an active state, commands may be allowed at step 1102. The transmitter 101 may then send glucose data during the active state to connected displays at step 1104.

At step 1106, the display may receive a calibration command from a user and provide the calibration command to the continuous glucose sensor system 100 at a specified time. The specified time can be when the transmitter 101 for the continuous glucose sensor system 100 enters an active state. Upon receiving the calibration command, the continuous glucose sensor system 100 may perform the requested calibration and calculated updated glucose values based on the new calibration at step 1108. In one embodiment, either the dedicated display 104*a* or the display 106*a* can provide the calibration command.

The calibration command may be provided by a user at any time. Alternatively, the calibration command may be provided in response to a prompt to the user. The continuous glucose sensor system 100 may record the last time that a calibration occurred and track when a defined amount of time has passed since a calibration. Upon passage of a certain amount of time, such as three weeks, the continuous glucose sensor system 100 may transmit a message to either the dedicated display, another display, or both prompting a user that it is time to perform another calibration. The continuous glucose sensor system 100 may also send a message prompting for calibration in response to detecting insertion or otherwise use of a new sensor 103. The message prompting for calibration may be considered an alarm, and the alarm may escalate over time. Ultimately, if the user does not perform a calibration, the continuous glucose sensor system 100 can transmit an error message to the displays indicating that the sensor 103 is out of calibration and the displayed values may not be accurate. In addition, glucose levels may stop being displayed until after successful calibration. In another embodiment, the display 106*a* or dedicated display 104*a* may track the last time a calibration was performed and prompt a user to perform a calibration once a defined amount of time has passed.

Next, the continuous glucose sensor system 100 may transmit the data relating to glucose levels based on the new calibration to both the display that requested a calibration and any other connected displays at step 1110. This transmission may occur even if a display has already received updated data relating to glucose levels in this communication interval. The data previously transmitted during a communication interval may be stored in addition to the new data, although, in one embodiment, the new data can be displayed to the user. For example, a user may initiate a calibration through dedicated display 104, and upon successful completion the continuous glucose sensor system 100 may send the updated data relating to glucose values to both dedicated display 104 and display 106 in the same communication interval. This avoids the issue of having one display present outdated data to a user. The order of generated glucose values may also be recorded so that only data values generated after the new calibration can be sent to the dedicated display 104*a* and display 106*a*. In other embodiments, the new and old data can be displayed to a user, with the old data being distinguished from new data such as through a label, shading, color, or other type of indication to a user that distinguishes the old data from new data. In addition, both new and old data can be collected and stored for later analysis and troubleshooting.

Figure 12:
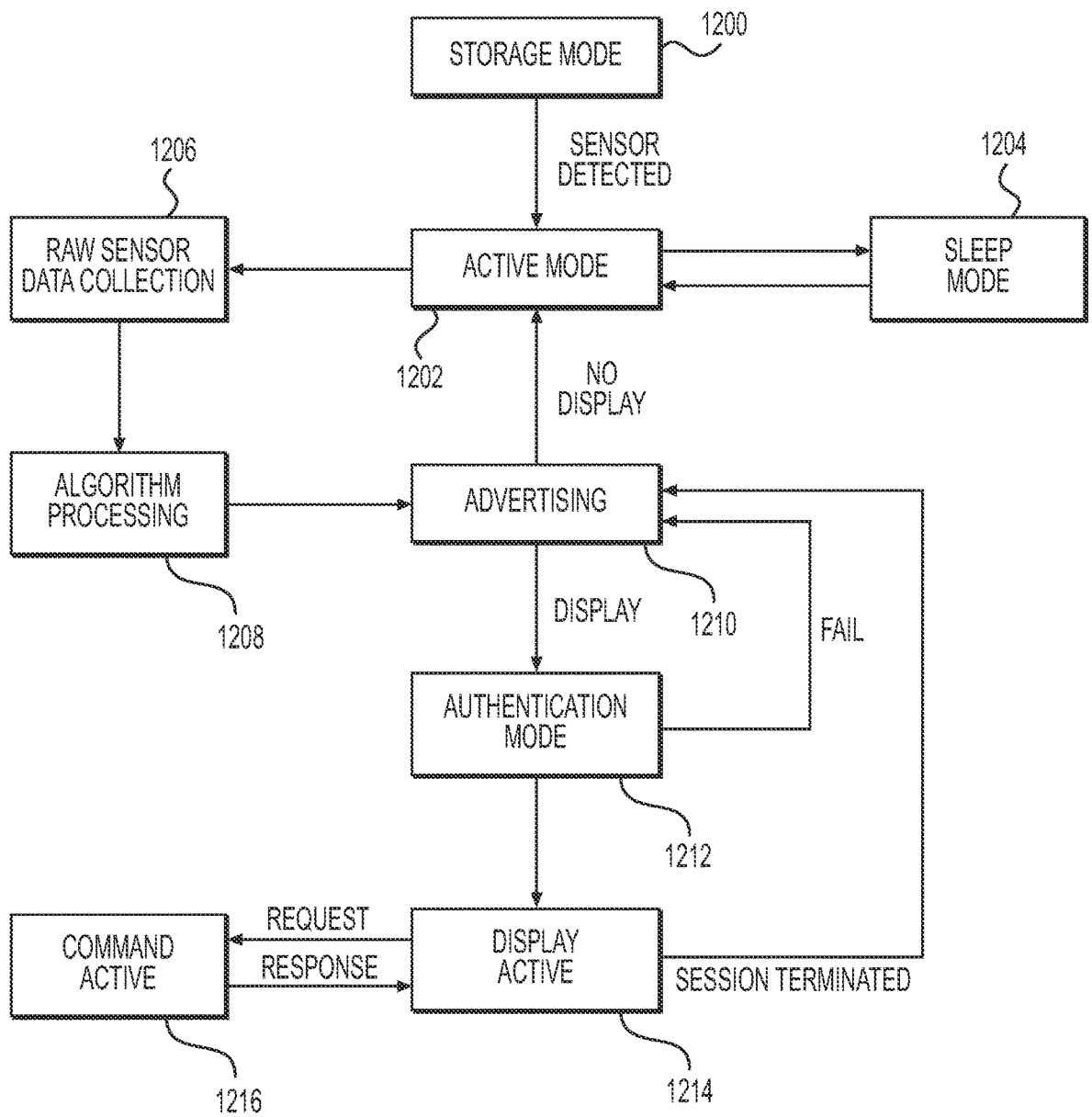
FIG. 12 illustrates an exemplary state diagram for a continuous glucose sensor and its transmitter connections.

FIG. 12 illustrates an exemplary state diagram for a continuous glucose sensor system 100 and its transmitter's connections. At 1200, the transmitter 101 may be in a storage mode prior to installation or use with the continuous glucose sensor system 100. The storage mode may be a mode the transmitter 101 is initially sold in and may include a low power consumption state. When the connection with the continuous glucose sensor system 100 is detected, the transmitter 101 may enter an active mode 1202 for future operation. Upon initial startup, the transmitter 101 may enter active mode 1202 automatically within a period of time, such as ten minutes, after being connected to an active continuous glucose sensor system 100. A new display may scan to identify a transmitter 101 becoming active for a period of time after a user enters the transmitter identifier using the display. In one example, the display may scan for ten minutes upon entry of a transmitter identifier, giving the user time to connect the transmitter 101 to the continuous glucose sensor system 100 and allow the transmitter 101 to activate.

As discussed previously, the transmitter 101 may periodically enter a sleep mode 1204 and emerge from the sleep mode back into the active mode 1202 at predetermined intervals. The transition to active mode may be done to accommodate raw sensor data collection 1206, which may be an ongoing process where the continuous glucose sensor system 100 takes a series of raw data values from a user. The raw data values may undergo algorithmic processing 1208 by the continuous glucose sensor system 100. The algorithmic processing may convert raw data values, such as voltages or current measurements, into familiar units of glucose levels, such as mg/dL, based on calibration values.

Periodically, the transmitter 101 may enter an advertising state 1210. The advertising state will advertise for any nearby displays that seek to connect with the continuous glucose sensor system 100 and receive data relating to glucose levels create by the algorithmic processing step 1208. The advertising state may continue for a period of time, such as seven seconds. If no display is detected during advertising, the transmitter 101 may terminate advertising and enter a sleep mode 1204 for a period of time, such as five minutes, until the next connection interval.

If, however, a display is detected in response to the advertising state 1210, an authentication mode 1212 occurs whereby the transmitter 101 engages in the authentication processes previously described. In particular, the display may validate the advertising packet by performing a hashing algorithm based on the transmitter identifier entered by the user. The authentication process also can include sending a challenge from the display to the transmitter 101 using the transmitter identifier and sending an application key request.

Additionally, a device type for the display can be sent to check against a whitelist. If authentication with a given display fails, such as when the display is not on the white list, does not successfully negotiate hashing algorithms or key exchange, or for other reasons, the transmitter 101 may resume an advertising state 1210 to determine if any other displays seek a connection.

If the authentication mode is successful, the transmitter 101 will enter a state acknowledging that a display is active for this session at 1214. While the display is active, it may send a command via a request to the transmitter 101. The transmitter 101 enters a command active state 1216 and processes the command, such as by undergoing a calibration process, and sends a response. After the command has been processed, the session may be terminated, causing the transmitter 101 to resume the advertising state for any other displays that seek communications. If none respond, the transmitter 101 will transition back to a sleep mode 1204 until the next active mode state 1202.

Figure 13:
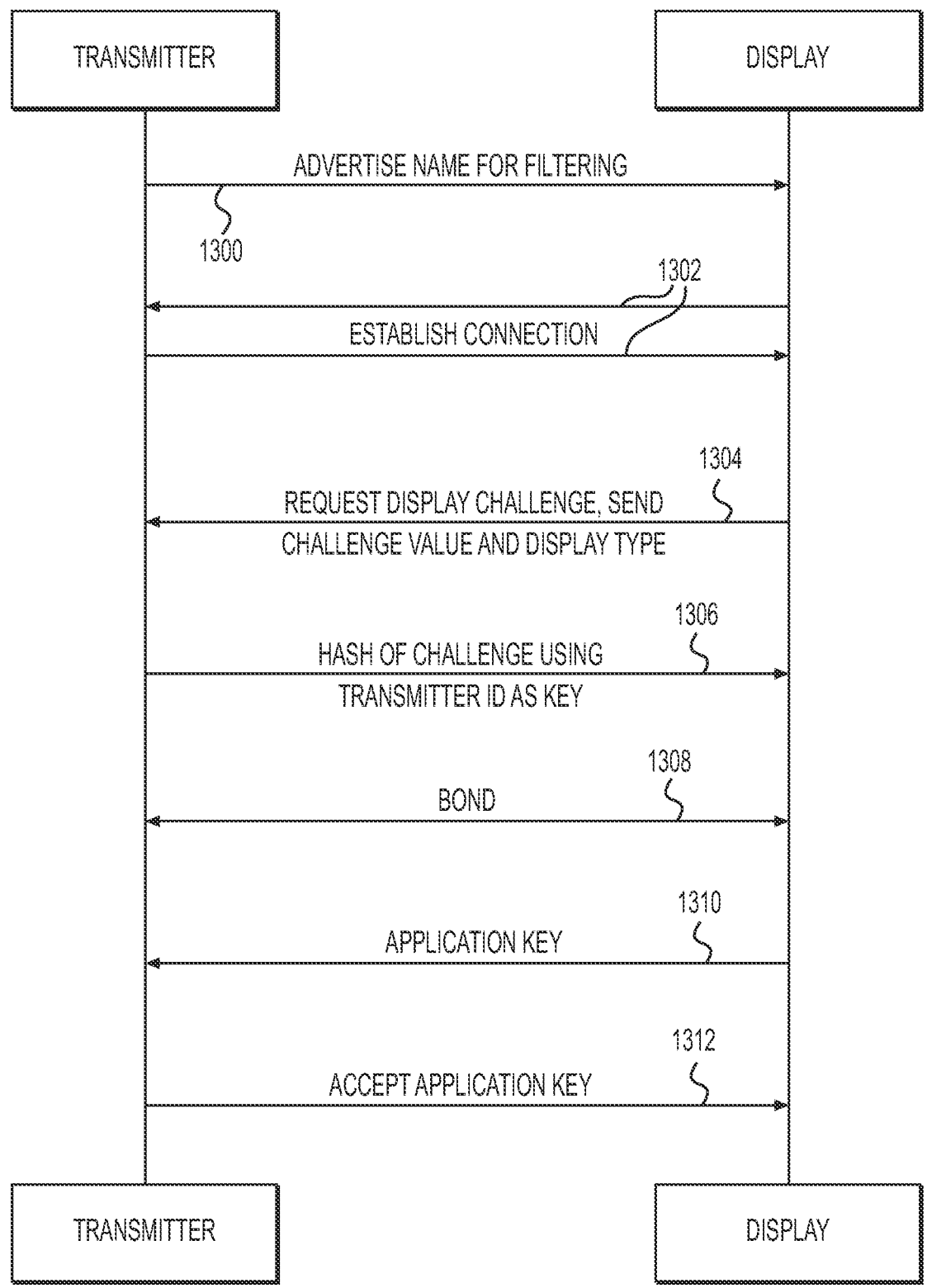
FIG. 13 illustrates an exemplary embodiment of communications between a continuous glucose sensor transmitter and a dedicated display or a display while authenticating and pairing.

FIG. 13 illustrates an exemplary embodiment of communications between a transmitter 101 and a dedicated display 104a or a display 106a while authenticating and pairing. FIG. 13 is an example of the implementation relating to FIG. 4 previously described. At step 1300, the transmitter 101 may advertise with packets that include the name of the transmitter to facilitate a connection. For example, the name of the transmitter may be displayed on the graphical user interface of a display for a user to select to proceed with a connection. In other embodiments, selection is not necessary because the connection process may proceed automatically.

At step 1302, the display and the transmitter 101 may establish an unsecured connection. The connection process involves the display validating the advertising packet that included the transmitter hashed value. The validation process may be executed using a hashing algorithm on a transmitter identifier entered by a user with the display. If the hashing values match, the connection process continues. If not, the connection process terminates.

At step 1304, the display requests a challenge by sending a challenge value. The challenge may use the transmitter identifier or an application key with a display type in the request. An error in the packet may result in an error response being returned from the transmitter. If the packet is received properly, the transmitter 101 and/or continuous glucose sensor system 100 can compute the hash using the display challenge value and, for example, an AES 128 algorithm that uses the transmitter identifier as a key.

Next, the transmitter 101 and/or continuous glucose sensor system 100 computes a hash value based on the display challenge value, with the transmitter identifier as a key, and sends the computed hash value back to the display at step 1306. The display compares the received transmitter hash value with the hash value computed by the display. If the two match, the connection sequence continues. If not, the connection terminates. The response to the challenge from the display can also include a challenge value from the transmitter 101. In this manner, the display may challenge the transmitter 101, and the transmitter 101 may challenge the display.

At step 1308, the transmitter 101 and display execute the bonding process. In one embodiment, the display may calculate a hash value based on the challenge value received from the transmitter 101, again using the transmitter identifier as a key. The display sends the computed hash value back to the transmitter 101. If any error is detected in the packet, an error response can be returned from the transmitter 101. If no error exists, the transmitter 101 compares the received hash value from the display with its own computed hash value. When the two hash values match, the sequence continues. Otherwise, the connection is terminated. At this point the display and the transmitter 101 have undergone two-way authentication and a secure connection is established. On the first connection, a short and long-term key may be exchanged. The pairing and bonding process is complete, and the bonding table or list can be updated with the bonding information, including the hashed values, keys, long-term key, short-term key, device types, and other values used to establish communications. Communications and transmission of data relating to glucose levels can now be sent to the display, and the display can send any commands or other information to the transmitter 101.

In one embodiment, the display can also send an application key to the transmitter 101 at step 1310. The transmitter 101 can initially use the transmitter identifier for the encryption key, but the key can be changed to strengthen application security. The transmitter identifier can be printed on the back of the transmitter 101, which can lead to it being compromised. Also, the transmitter identifier remains the same value over time, so it is subject to repeated attacks over time. Switching to an application key provides enhanced security and the ability to change the key over time. The application key can be sent over a secure link that employs encryption, such as Bluetooth encryption.

The display can store the application key and the prior application key in permanent, non-volatile memory. The transmitter 101 records the new application key and sends an indication back to the display that the application key was accepted at step 1312. Upon receiving a response indicating the application key was accepted, the transmitter 101 can, in one embodiment, delete the old application key. Communications can also be tested using the new application key prior to deleting the old application key. If the display does not receive a response indicating acceptance of the application key, it keeps the old application key and the new application key. On the next communication cycle when the transmitter 101 enters the awake state, the display may first attempt to use communications with the new application key. If successful, the old application key may be deleted. If not, communications may continue with the old application key, and the display may reinitiate the process of sending the transmitter 101 a new application key.

Figure 14:
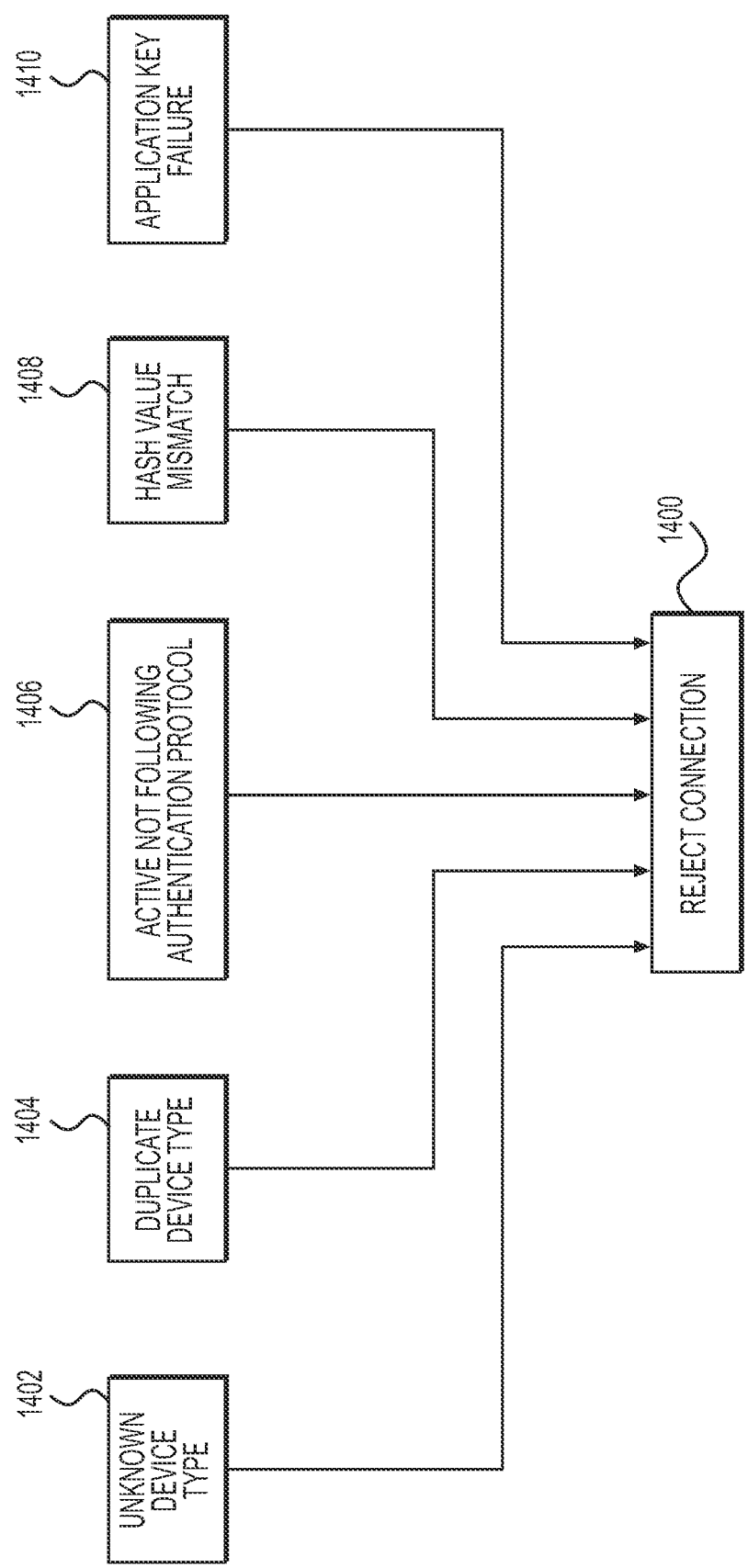
FIG. 14 illustrates exemplary use cases in which a connection can be rejected.

FIG. 14 illustrates exemplary use cases in which a connection can be rejected. One example is when an unknown device type attempts to connect with a continuous glucose sensor system 100, as shown at 1402. The device type may be a unique value designed for exchange with the continuous glucose sensor system 100. As a result, a display that sends a device type not conforming the expected values will have its connection request rejected at 1400.

Another example is when a duplicate device type occurs at 1404. In one embodiment, only one device for a dedicated display 104a and one display 106a can connect during each communication interval. Although a user may have, for example, two smartphones, each of which can connect with the continuous glucose sensor system 100, only one connection with that device type can be allowed in a given communication interval. The second device having a duplicate device type can have its connection request rejected.

A device that is actively and has previously connected with the continuous glucose sensor system 100 can also be rejected when it does not follow the authentication protocol, as shown at 1406. In one embodiment, displays can be required to follow the authentication protocol for every communication interval and corresponding connection request. A device that is active and included in the white list can still be rejected if it attempts to bypass the authentication protocol.

Another example of rejecting a connection request involves a hash value mismatch 1408. The hash value mismatch can occur in either step of the two-way authentication process, causing the continuous glucose sensor system 100 to reject that connection request for a given communication interval. Finally, another example involves repeated application key failure at 1410. If authentication fails with an application key, the display can disconnect from the transmitter 101 and reject the connection. This process can repeat in the next communication interval. On the third cycle, the display can attempt to connect with the application key again, and if that fails, it can revert to using the transmitter identifier as the key to authenticate. The display can then establish and exchange a new application key.

Figure 15:
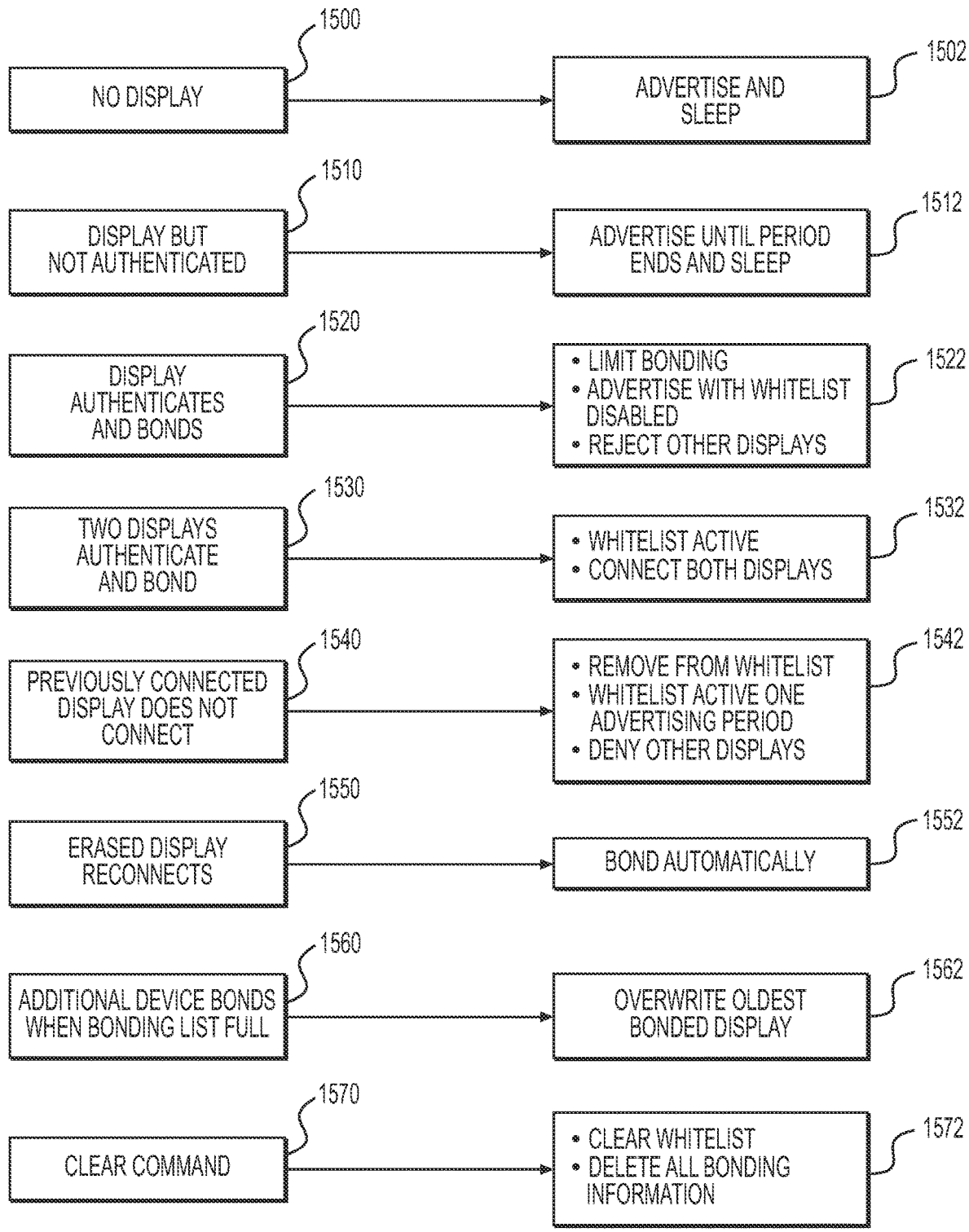
FIG. 15 illustrates exemplary use cases for connecting displays.

FIG. 15 illustrates exemplary use cases for connecting displays. In a first example, no display may be in the area at 1500, so the transmitter 101 may advertise for one period and then resume the sleep state at 1502. If a display is in the wireless communication range at 1510, but the display is not authenticated properly within the allotted time, the transmitter 101 may resume the advertising state provided the advertisement period (such as 7 seconds) has not yet expired. After there is an advertisement timeout, the transmitter 101 will go to the sleep state at 1512.

If a display is in the vicinity that authenticates correctly and bonds with the transmitter at 1520, the transmitter 101 may limit bonding after authentication and take other actions shown at 1522. In particular, after authentication, bonding can be available only for the type of display that is currently connected. After a connection timeout or disconnection, the transmitter 101 can resume the advertising state, in the same communication interval, with the whitelist filter disabled. On the next communication interval, the whitelist filter can be active for the first advertising period. Then, the whitelist filter can be disabled for the second advertising period. When the whitelist filter is enabled, other un-bonded displays can be rejected and the transmitter 101 can transition to the advertising state.

If two displays authenticate correctly and bond with the transmitter 101 at step 1530, the transmitter 101 may have the whitelist active and connect both displays at 1532. In particular, the whitelist filter can be active for the two advertising periods per communication interval. Both bonded displays are allowed to connect to the transmitter 101 in the same communication interval. When the whitelist filter is enabled, other un-bonded displays are rejected and the transmitter 101 transitions to the advertising state.

If a previously connected and bonded display does not connect to the transmitter 101 for a given number of communication intervals at 1540, such as two intervals, the previously connected display can be removed from the whitelist at 1542. The bonding information of the absent display can be retained in the bonding list. In this example, the whitelist filter can be active for the first advertising period to give preference to the already bonded display. The whitelist filter can be disabled for the second communication interval to allow another display to connect and authenticate. Once the allowed bond for a given type of display is taken, another display of the same type will be denied bonding even if it authenticates properly. After this denial, the transmitter 101 can go to the advertising state provided the advertisement period has not expired yet.

If a previously bonded display, such as a smart phone, that was erased from the whitelist attempts to reconnect at 1550, the previously bonded display will not have to manually accept the bond request provided it is still in the bonding list. Bonding instead proceeds automatically at 1552.

If an additional device bonds when the bonding list is full at 1560, the bonding information for the oldest bonded display can be overwritten at 1562. In one embodiment, the bonding list can maintain a circular queue that stores up to three displays. When an additional display bonds and the queue is full, the transmitter 101 can overwrite the oldest bonding information.

At 1570, a clear command can also be provided from an authenticated and bonded display to deletes all bonds. The transmitter 101 can clear the whitelist and delete all bonding information at 1572 in response to the clear command.

Figure 16:
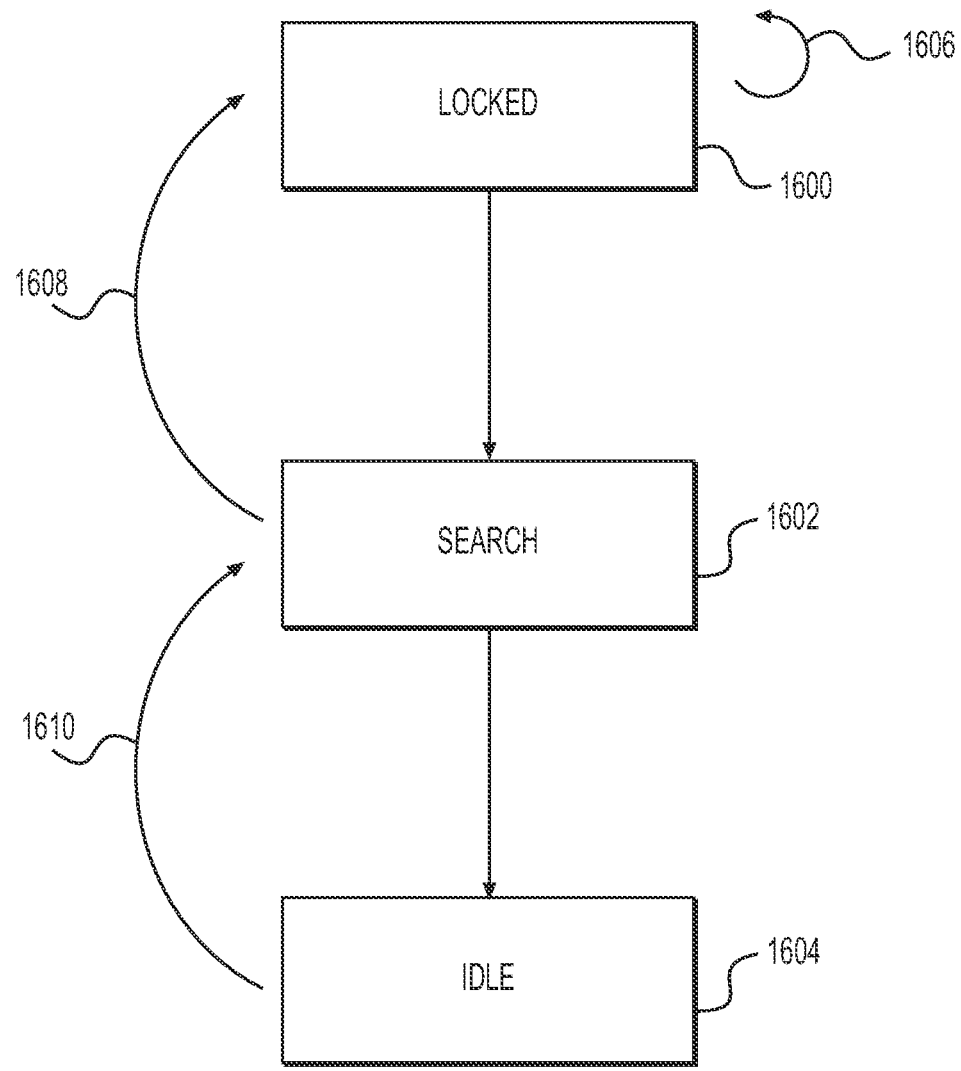
FIG. 16 illustrates an exemplary state diagram for a dedicated display.

FIG. 16 illustrates an exemplary state diagram for a dedicated display 104*a* and/or a display 106*a*. One issue that arises is transitioning the display in and out of various states during use, such as an idle state between communication intervals, a state of searching for available connections, and an active state of data transmissions. The method of FIG. 16 illustrates these transitions between various states consistent with certain embodiments.

At 1600, the display may be in a locked state. In the locked state, the display has successfully connected and paired with a transmitter 101. A synchronization characteristic can be shared between the two devices, allowing them to coordinate the next advertising event. In this state, the display will not have any radio activity with the continuous glucose sensor/transmitter between each connection cycle, which may occur approximately every 5 minutes. During this state, the display can scan for a period of time, such as twenty-five seconds, to reconnect to the transmitter 101. In addition, an additional lead time, such as 500 ms, can be added for additional scanning before the coordinated advertisement event. If the display does not connect to the transmitter 101 on the first attempt, it can retry at five minute intervals from the original coordinated advertisement event. After thirty minutes of not finding the transmitter 101, the display can fall out of locked state and into search state at 1602. In addition, the display can transition from a locked to a search state if a user changes the transmitter identifier, indicating a new transmitter has entered the system.

In the search state 1602, the display can scan frequently to discover the transmitter 101. For example, the display can scan for twenty-five seconds followed by five seconds of no radio activity. If no transmitter 101 is discovered after five minutes, the display can enter an idle state at 1604. If the transmitter 101 is connected and bonded, the locked state will be entered as shown at 1608. The search state can also continue where the transmitter identifier is changed by a user, a start sensor session command is received, or when a user wakes up the screen or executes the application for glucose monitoring.

The display can enter an idle state 1604 if the display has not discovered the desired transmitter 101 in the search state. During this time, there may not be any radio activity. After a period of time, such as one hour, the display can re-enter the search state as shown at 1610. A transition to the search state may also occur if user driven commands are received, such as a command to set or update a transmitter identifier, start a sensor session, or when a user wakes up the screen or executes the application for glucose monitoring.

Figure 17:
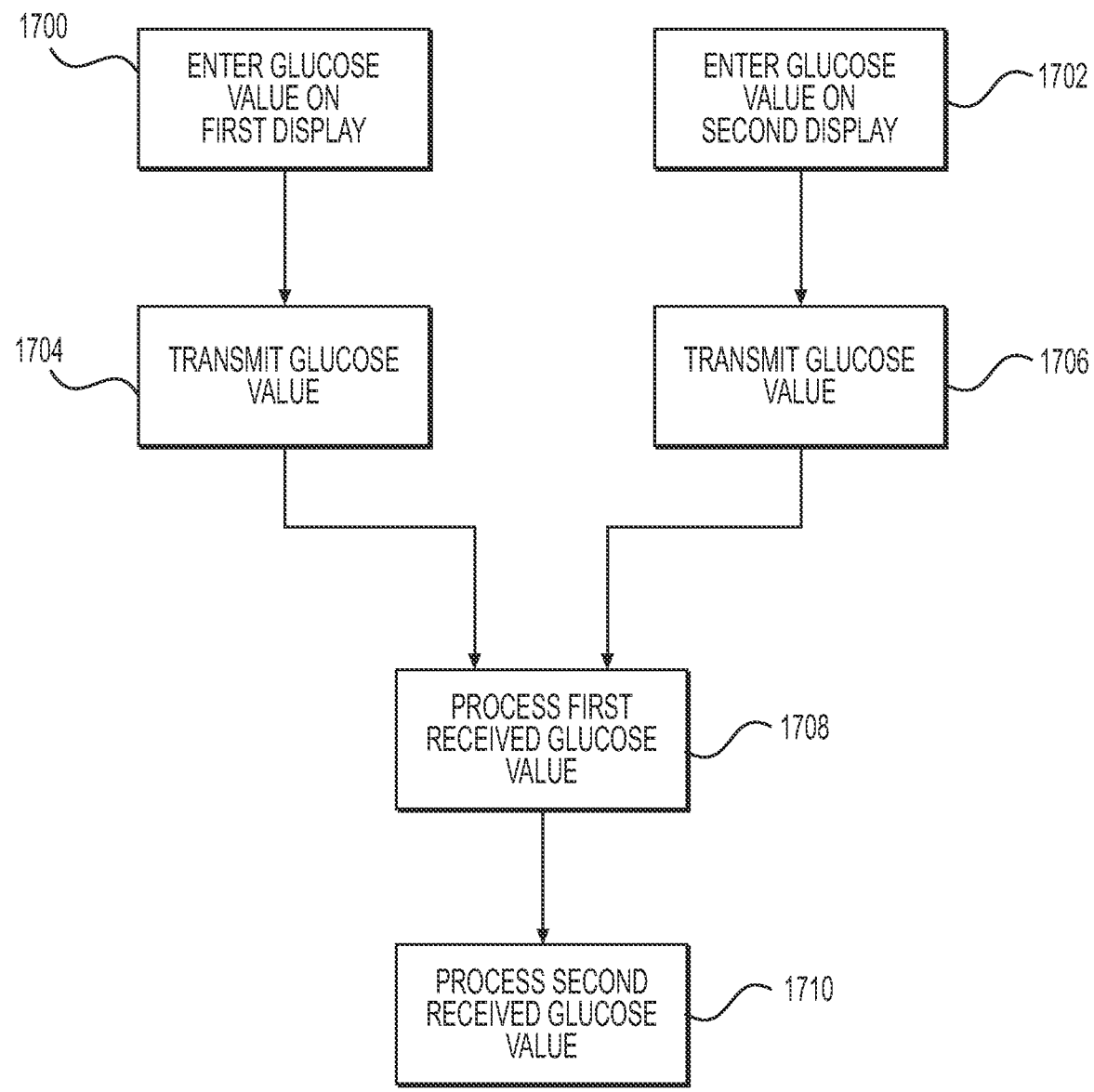
FIG. 17 illustrates an exemplary method for calibrating a continuous glucose sensor with multiple displays.

Reference will now turn to FIG. 17, which illustrates an exemplary method for calibrating a continuous glucose sensor system 100 with multiple displays. The continuous glucose sensor system 100 may include a sensor 103 or other device for sampling data relating to glucose levels from the body. The sensor 103 may need replaced periodically, and part of the replacement process involves calibrating a new sensor 103. The calibration process may occur, for example, using a blood glucose measurement that is taken using another measurement device, such as a single point blood glucose finger stick meter. A user may stop their old sensor, insert a new sensor, and reconnect the new sensor to the transmitter. Once the new sensor has been inserted, the user may use either dedicated display 104a or display 106a to start the new sensor, enter a warm-up period, and perform calibration.

Once the warm-up period is complete, the continuous glucose sensor system 100 may transmit a message to the dedicated display 104a and display 106a to prompt a user to perform a calibration. The user may take their blood glucose level using a blood glucose meter and enter the value into the dedicated display 104a or display 106a to initiate calibration of the sensor 103. In some implementations, the display transmits the calibration value to the continuous glucose sensor system 100 and the continuous glucose sensor system 100 algorithmically processes the calibration value to calibrate the sensor 103 and generate calibrated sensor data. This process may occur multiple times during a session using the sensor 103, so that two blood glucose calibration values may be used to obtain a higher accuracy in the calibration.

In FIG. 17, a user may choose to perform the calibration process with either display, and may sometimes enter a value into both displays. The method of FIG. 17 processes the received calibration values and coordinates the calibration values between the continuous glucose sensor system 100 and both of the displays.

At step 1700, a user may enter a blood glucose value on a first display, such as dedicated display 104a. The blood glucose value may be obtained using a single point blood glucose meter. The first display may be updated to indicate the calibration value was received. Optionally, the user may also enter the same value on a second display, such as display 106a, at step 1702. The second display may also be updated to indicate the calibration value was received. Each of the displays may transmit the glucose value to the continuous glucose sensor system 100 at steps 1704 and 1706.

At step 1708, the continuous glucose sensor system 100 processes the first received glucose value. The transmitter 101 and/or continuous glucose sensor system 100 performs calibration using the first blood glucose value that was received and returns an updated glucose value, trending arrow, and estimated error range to the display that sent the first blood glucose value. The second received glucose value may then be processed at step 1710. In one embodiment, the second received blood glucose value from the second display may not be used, and instead the transmitter 101 can send a message to the second display indicating that calibration was already performed on another device. The second display may then request the updated values and the transmitter 101 will return the current glucose levels, trending arrow, and other data relating to glucose levels to the second display. At this point, the second display will be updated to show the same information as the first display.

In some embodiments, the glucose values from the first and second display need not be the same. The user may take multiple measurements and enter the blood glucose calibration values on multiple displays. Still, the first-received blood glucose value within a time interval, such as ten minutes, can be used and the second-received blood glucose value may be ignored by the transmitter 101. In some embodiments, the second-received blood glucose value can be used, even when it was provided within the time interval, when the second-received blood glucose value differs from the first-received blood glucose value by a defined amount. This may indicate that an error occurred with taking the first-received blood glucose value. For example, if the first-received blood glucose value and the second-received blood glucose value differ by more than 20 mg/dL, the second-received blood glucose value may be used to calibrate, either instead of or in addition to the first-received blood glucose value.

In another embodiment, a user may enter a blood glucose value on the first and second display, and the first display sends its blood glucose value to the transmitter 101. The transmitter 101 sends a blood glucose acknowledgment to the first display, but it may indicate an error or failure in the calibration process. The first display may then request data relating to glucose values and receive an indication that calibration failed. The first display therefore can update the display to reflect that calibration is still required due to the error status. Subsequently, the second display can send its blood glucose value to the transmitter 101, which will note that the blood glucose value is a duplicate of the value already received from the first display. The second display will receive an indication that calibration failed in response to a request for data relating to glucose levels. The user may then re-enter the blood glucose value on one or both of the displays, which may cause the process of FIG. 17 to perform again, this time resulting in accepted values and successful calibration.

The user need not enter the blood glucose value on both displays. For example, where a single display is used, the calibration can occur and be successful, resulting in the updated data relating to glucose values being displayed on both displays. In one embodiment, a second display may receive data relating to glucose values, then the first display can be used to start the calibration process. The first display may perform calibration and show updated values while the second display waits until another communication interval to receive updated data relating to glucose values. The two displays will therefore show the same values after the next communication interval.

Figure 18:
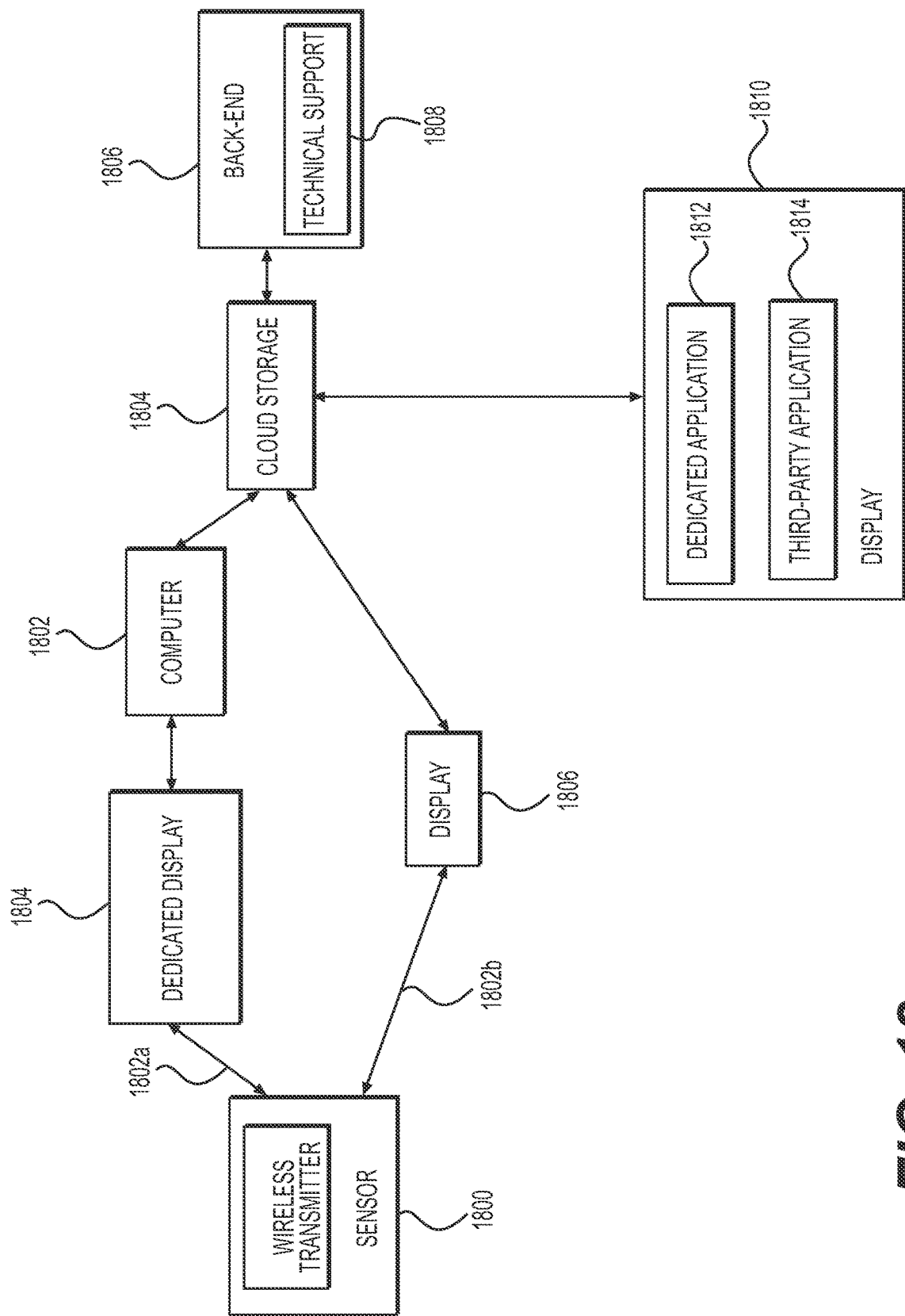
FIG. 18 illustrates an exemplary system for monitoring glucose levels.

FIG. 18 illustrates an exemplary system for monitoring glucose levels. The system of FIG. 18 may be used in conjunction with the previously described embodiments. The system may include a continuous glucose sensor system 1800, wireless connections 1802a-b, dedicated display 1804, and a display 1806 executing applications. The dedicated display 1804 may be connected using either a wired or wireless connection to computer 1802. Computer 1802 may be, for example, a personal computer, tablet, laptop, smart phone, or server. In addition, dedicated display 1804 may connect to display 1806, and display 1806 may connect to computer 1802.

Computer 1802 and display 1806 may connect to cloud storage 1804, which may provide long-term storage of data relating to glucose values, health information, system calibrations, and other information relating to continuous glucose monitoring. Cloud storage 1804 may include a plurality of storage devices, computers, and network connections. Communications between dedicated display 104, computer 1802, display 106, and cloud storage 1804 may use encryption to prevent unauthorized access to medical data.

Cloud storage 1802 may connect to a back-end system 1806. The back-end system 1806 may provide technical support 1808 for a user in configuring and using the continuous glucose monitor. The back-end system 1806 may also monitor system information, such as versions of software executing on continuous glucose sensor system 1800, dedicated display 1804, display 1806, and computer 1802. Updates may be provided on demand or pushed to a user using network connections in a secure fashion.

Another display 1810 may also connect to cloud storage 1802. The display 1810 may include a dedicated application 1812 and one or more third-party applications 1814, which can be used to monitor and display glucose values. A user of continuous glucose sensor system 1800 may allow additional people to monitor their glucose levels and other health information. For example, a child may wear the continuous glucose monitor and have an associated dedicated display 1804 and display 1806. The child may designate one or both of their parents as additional users who can access the child's glucose levels and other health information using display 1810. The display 1810 may be, for example, the parent's smart phone.

The continuous glucose data may be provided to cloud storage 1804 and monitored by cloud storage 1804, back-end 1806, and/or display 1802. The display 1802 may receive and display continuous glucose values as described previously, either without restriction or subject to restrictions as with third-party applications. The restrictions may be set by the user of the continuous glucose monitor in some embodiments. In other embodiments, the user of display 1810 may set any restrictions for data it receives through an authenticated process between the user of continuous glucose sensor system 1800, the user of display 1810, and back-end 1806. For example, the users may call the back-end and answer security questions before establishing the appropriate operation of the system, or this process may be completed online. Once complete, the user of continuous glucose sensor system 1800 or the user of display 1810 may be restricted in the data their device receives or their ability to change system operation. This can prevent a user of continuous glucose sensor system 1800 from restricting monitoring by display 1810, such as when a child may eat a lot of sweet food at a birthday party that can cause a spike in glucose levels.

Figure 19:
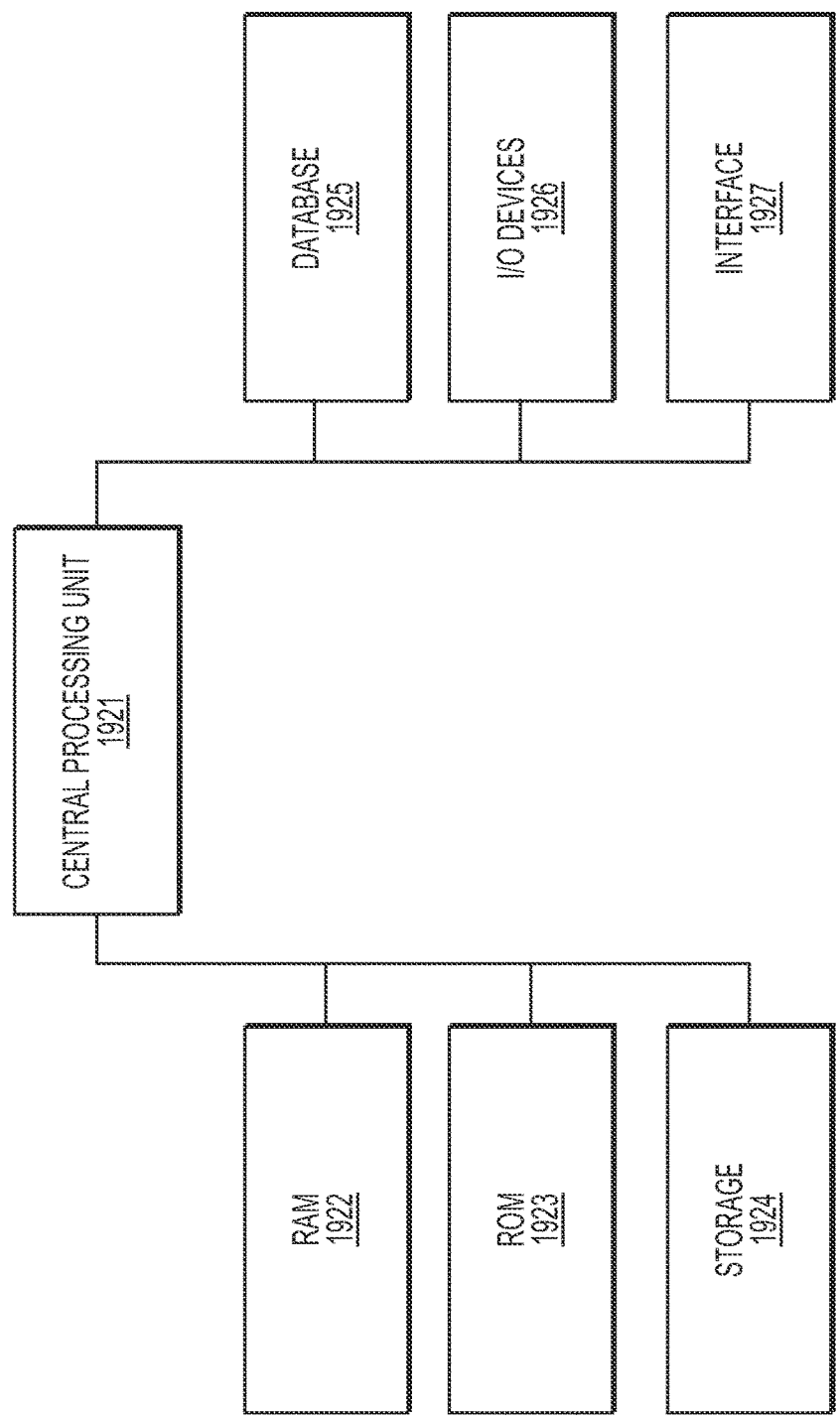
FIG. 19 illustrates an exemplary computer for monitoring glucose levels.

FIG. 19 illustrates an exemplary computer for monitoring glucose levels. Continuous glucose sensor system 1800, dedicated display 104a, display 106a, computer 1802, cloud storage 1804, back-end 1806, and display 1810 may all include the components shown in FIG. 19.

The computers may include one or more hardware components such as, for example, a central processing unit (CPU) 1921, a random access memory (RAM) module 1922, a read-only memory (ROM) module 1923, a storage 1924, a database 1925, one or more input/output (I/O) devices 1926, and an interface 1927. Alternatively and/or additionally, the computer may include one or more software components such as, for example, a computer-readable medium including computer executable instructions for performing a method associated with the exemplary embodiments. It is contemplated that one or more of the hardware components listed above may be implemented using software. For example, storage 1924 may include a software partition associated with one or more other hardware components. It is understood that the components listed above are exemplary only and not intended to be limiting.

CPU 1921 may include one or more processors, each configured to execute instructions and process data to perform one or more functions associated with a computer for monitoring glucose levels. CPU 1921 may be communicatively coupled to RAM 1922, ROM 1923, storage 1924, database 1925, I/O devices 1926, and interface 1927. CPU 1921 may be configured to execute sequences of computer program instructions to perform various processes. The computer program instructions may be loaded into RAM 1922 for execution by CPU 1921.

RAM 1922 and ROM 1923 may each include one or more devices for storing information associated with operation of CPU 1921. For example, ROM 1923 may include a memory device configured to access and store information associated with controller 1920, including information for identifying, initializing, and monitoring the operation of one or more components and subsystems. RAM 1922 may include a memory device for storing data associated with one or more operations of CPU 1921. For example, ROM 1923 may load instructions into RAM 1922 for execution by CPU 1921.

Storage 1924 may include any type of mass storage device configured to store information that CPU 1921 may need to perform processes consistent with the disclosed embodiments. For example, storage 1924 may include one or more magnetic and/or optical disk devices, such as hard drives, CD-ROMs, DVD-ROMs, or any other type of mass media device.

Database 1925 may include one or more software and/or hardware components that cooperate to store, organize, sort, filter, and/or arrange data used by CPU 1921. For example, database 1925 may data relating to monitoring glucose levels, associated metadata, and health information. It is contemplated that database 1925 may store additional and/or different information than that listed above.

I/O devices 1926 may include one or more components configured to communicate information with a user associated with controller 1920. For example, I/O devices may include a console with an integrated keyboard and mouse to allow a user to maintain a database of images, update associations, and access digital content. I/O devices 1926 may also include a display including a graphical user interface (GUI) for outputting information on a monitor. I/O devices 1926 may also include peripheral devices such as, for example, a printer for printing information associated with controller 1920, a user-accessible disk drive (e.g., a USB port, a floppy, CD-ROM, or DVD-ROM drive, etc.) to allow a user to input data stored on a portable media device, a microphone, a speaker system, or any other suitable type of interface device.

Interface 1927 may include one or more components configured to transmit and receive data via a communication network, such as the Internet, a local area network, a workstation peer-to-peer network, a direct link network, a wireless network, or any other suitable communication platform. For example, interface 1927 may include one or more modulators, demodulators, multiplexers, demultiplexers, network communication devices, wireless devices, antennas, modems, and any other type of device configured to enable data communication via a communication network.

Any combination of one or more computer readable medium(s) may be utilized. The computer readable medium may be a computer readable signal medium or a computer readable storage medium. A computer readable storage medium may be, for example, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. Program code embodied on a computer readable medium may be transmitted using any appropriate medium, including but not limited to wireless, wireline, optical fiber cable, RF, etc., or any suitable combination of the foregoing.

Computer program code for may be written in any combination of one or more programming languages, including an object oriented programming language such as Java, Smalltalk, C++, or the like, and conventional procedural programming languages, such as the "C" programming language or similar programming languages. The program code may execute entirely on the computing unit.

It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

Although the term first application has been referred to as dedicated application 108, it will be appreciated that a first application may be any of third party application 110~116 or another application. Similarly, while the second application has been referred to as approved third-party application 110 and a health application, the second application may also be dedicated application 108, any of third party applications 112~116, or another application. Moreover, while certain applications 110~116 have been described as third-party applications, it will be appreciated that applications 110~116 need not be provided by third-parties.

It should be understood that the various techniques described herein may be implemented in connection with hardware or software or, where appropriate, with a combination thereof. Thus, the methods and apparatuses of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or utilize the processes described in connection with the presently disclosed subject matter, e.g., through the use of an application programming interface (API), reusable controls, or the like. Such programs may be implemented in a high level procedural or object-oriented programming language to communicate with a computer system. However, the program(s) can be implemented in assembly or machine language, if desired. In any case, the language may be a compiled or interpreted language and it may be combined with hardware implementations.

While this specification contains many specific implementation details, these should not be construed as limitations on the claims. Certain features that are described in this specification in the context of separate implementations may also be implemented in combination in a single implementation. Conversely, various features that are described in the context of a single implementation may also be implemented in multiple implementations separately or in any suitable subcombination. Moreover, although features may be described above as acting in certain combinations and even initially claimed as such, one or more features from a claimed combination may in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems may generally be integrated together in a single software product or packaged into multiple software products.

It should be appreciated that the logical operations described herein with respect to the various figures may be implemented (1) as a sequence of computer implemented acts or program modules (i.e., software) running on a computing device, (2) as interconnected machine logic circuits or circuit modules (i.e., hardware) within the computing device and/or (3) a combination of software and hardware of the computing device. Thus, the logical operations discussed herein are not limited to any specific combination of hardware and software. The implementation is a matter of choice dependent on the performance and other requirements of the computing device. Accordingly, the logical operations described herein are referred to variously as operations, structural devices, acts, or modules. These operations, structural devices, acts and modules may be implemented in software, in firmware, in special purpose digital logic, and any combination thereof. It should also be appreciated that more or fewer operations may be performed than shown in the figures and described herein. These operations may also be performed in a different order than those described herein.

What is claimed is:

1. An analyte sensor system, comprising:
   an analyte sensor configured to generate an electrical current indicative of an analyte measurement;
   a sensor electronics module, comprising:
      a transceiver;
      a memory comprising executable instructions;
      a processor in data communication with the transceiver and memory and configured to execute the executable instructions in the memory to cause the analyte sensor system to:
         establish, via the transceiver, a first wireless connection with a first medical device;
         subsequent to establishing the first wireless connection, remove the first medical device from a list of authorized devices that are permitted to wirelessly communicate with the analyte sensor system;
         authenticate a second medical device of the same type as the first medical device;

add the second medical device to the list of authorized devices; and subsequent to the adding, establish, via the transceiver, a second wireless connection with the second medical device.

2. The analyte sensor system of claim 1, wherein the processor being configured to cause the analyte sensor system to remove the first medical device from the list of authorized devices further comprises the processor being configured to cause the analyte sensor system to remove bonding information associated with the first medical device.

3. The analyte sensor system of claim 1, wherein the list of authorized devices comprises at least one of a whitelist or a list of bonded devices.

4. The analyte sensor system of claim 1, wherein the analyte monitoring system is a continuous analyte monitoring system.

5. The analyte sensor system of claim 1, wherein the removal of the first medical device from the list of authorized devices is in response to a request.

6. The analyte sensor system of claim 5, wherein the request is received from the first medical device.

7. The analyte sensor system of claim 5, wherein the request to remove the first medical device is provided by a user through a user interface on a third device and received by the analyte monitoring system from the third device.

8. The analyte sensor system of claim 7, wherein:
the processor is further configured to cause the analyte monitoring system to provide the list of authorized devices to the third device, and
the request to remove the first medical device through the user interface on the third device comprises a selection of the first medical device from the list of authorized devices for removal.

9. The analyte sensor system of claim 5, wherein the removal of the first medical device from the list of authorized devices is performed automatically.

10. The analyte sensor system of claim 1, wherein at a time of the removal of the first medical device, the first medical device has not communicated with the analyte monitoring system for at least one of a defined period of time or a connection interval.

11. The analyte sensor system of claim 1, wherein bonding information associated with the first medical device is:
retained after the first medical device is removed from the list of authorized devices, and
used for reconnection.

12. The analyte sensor system of claim 1, wherein the type of the first medical device is a dedicated display device.

13. The analyte sensor system of claim 1, wherein the type of the first medical device is a class III medical device.

14. A method of wireless communication for use by an analyte sensor system, comprising:

establishing a first wireless connection with a first medical device;

subsequent to establishing the first wireless connection, removing the first medical device from a list of authorized devices that are permitted to wirelessly communicate with the analyte sensor system;

authenticating a second medical device of the same type as the first medical device;

adding the second medical device to the list of authorized devices; and subsequent to the adding, establishing a second wireless connection with the second medical device.

15. The method of claim 14, wherein removing the first medical device from the list of authorized devices comprises removing bonding information associated with the first medical device.

16. The method of claim 14, wherein the list of authorized devices comprises at least one of a whitelist or a list of bonded devices.

17. The method of claim 14, wherein the analyte monitoring system is a continuous analyte monitoring system.

18. The method of claim 14, wherein removing the first medical device from the list of authorized devices is in response to a request.

19. The method of claim 18, further comprising:
receiving the request from the first medical device.

20. The method of claim 18, wherein the request to remove the first medical device is provided by a user through a user interface on a third device and received by the analyte monitoring system from the third device.

21. The method of claim 20, further comprising providing the list of authorized devices to the third device, and wherein the request to remove the first medical device being provided through the user interface on the third device comprises a selection of the first medical device from the list of authorized devices for removal.

22. The method of claim 18, wherein the removing of the first medical device from the list of authorized devices is performed automatically.

23. The method of claim 14, wherein at a time of the removing of the first medical device, the first medical device has not communicated with the analyte monitoring system for at least one of a defined period of time or a connection interval.

24. The method of claim 14, wherein bonding information associated with the first medical device is:
retained after the first medical device is removed from the list of authorized devices, and
used for reconnection.

25. The method of claim 14, wherein the type of the first medical device is a dedicated display device.

26. The method of claim 15, wherein the type of the first medical device is a class III medical device.

* * * * *